(12) United States Patent
Szabo et al.

(10) Patent No.: US 6,900,197 B2
(45) Date of Patent: May 31, 2005

(54) COBALT-PORPHYRIN COMPLEXES AND USE THEREOF AS AN ANTI-OBESITY AGENT

(75) Inventors: Tomas R. Szabo, San Diego, CA (US); Soumitra S. Ghosh, San Diego, CA (US); Robert E. Davis, San Diego, CA (US)

(73) Assignee: MitoKor, San Diego, CA (US)

( * ) Notice: Subject to any disclaimer, the term of this patent is extended or adjusted under 35 U.S.C. 154(b) by 82 days.

(21) Appl. No.: 10/020,867

(22) Filed: Dec. 14, 2001

(65) Prior Publication Data

US 2002/0165216 A1 Nov. 7, 2002

Related U.S. Application Data

(60) Provisional application No. 60/255,960, filed on Dec. 15, 2000.

(51) Int. Cl.$^7$ .................... A61K 31/555; A61K 31/415; A61K 31/40
(52) U.S. Cl. ...................... 514/185; 514/396; 514/397; 514/410; 540/145
(58) Field of Search ............................... 514/185, 410, 514/396, 397; 540/145

(56) References Cited

U.S. PATENT DOCUMENTS

| | | | | |
|---|---|---|---|---|
| 4,675,338 A | * | 6/1987 | Bommer et al. | 514/410 |
| 4,948,792 A | | 8/1990 | Kappas et al. | 514/185 |
| 5,084,475 A | | 1/1992 | Kappas et al. | 514/410 |
| 5,149,697 A | | 9/1992 | Johnson et al. | 514/185 |
| 5,192,757 A | | 3/1993 | Johnson et al. | 514/185 |
| 5,275,801 A | * | 1/1994 | Niedballa et al. | 424/9.362 |
| 5,929,064 A | * | 7/1999 | Goel et al. | 514/185 |
| 6,136,841 A | * | 10/2000 | Platzek et al. | 514/410 |

FOREIGN PATENT DOCUMENTS

WO  WO 97/05152  2/1997

OTHER PUBLICATIONS

Markush Chemical Structure Search Results for Porphyrin Type Compound with isopropyl group, Chemical Abstracts Service MARPAT Database, Feb. 24, 2003. (Previously listed on applicants' 1449, now considered by the examiner).*
Choi et al., "Weight loss in rats treated with intracerebroventricular cobalt protoporphyrin is not specific to the neuropeptide Y system," *Brain Research* 729(2):223–227, Aug. 12, 1996.
Galbraith and Kappas, "Cobalt–protoporphyrin suppresses expression of genetic obesity in homozygous (fa/fa) Zucker rats," *Pharmacology* 41(5):292–298, 1990.
Galbraith and Kappas, "Regulation of food intake and body weight by cobalt porphyrins in animals," *P.N.A.S. USA* 86(19):7653–7657, Oct. 1989.

Sies, "Ebselen, a selenoorganic compound as glutathione peroxidase mimic," *Free Radical Biology Medicine* 14(3):313–323, Mar. 1993.
Tomaro et al., "Heme oxygenase induction by $CoCl_2$, Co–protoporphyrin IX, phenylhydrazine, and diamide: evidence for oxidative stress involvement," *Arch. Biochem. Biophys.* 286(2):610–617, May 1, 1991.
Turner et al., "Lack of NPY–induced feeding in cobalt protoporphyrin–treated rats is a postreceptor defect," *Physiology Behavior* 56(5):1009–1014, Nov. 1994.
Markush Chemical Structure Search Results for Porphyrin Type Compound with isopropyl group, Chemical Abstract Service MARPAT Database, Feb. 24, 2003.
Amersi et al., "Upregulation of heme oxygenase–1 protects genetically fat Zucker rat livers from ischema/reperfusion injury," *Journal of Clinical Investigation* 104(11):1631–1639, Dec. 1999.
Dickinson and Chien, "Model System of Cobalt–Cytochrome c," *Inorganic Chemistry* 15(5):1111–1114, 1976.
Dickinson and Symons, "Electron Spin Resonance Monitoring of Ligand Ejection Reactions Following Solid–State Reduction of Cobalt Globin and Cobalt Protoporphyrin Complexes," *Journal of Physical Chemistry* 86:917–921, 1982.
Hoffman et al., "Quantitation of a novel metalloporphyrin drug in plasma by atomic absorption spectroscopy," *Journal of Pharmaceutical Biomedical Analysis* 19(3–4):319–326, Mar. 1999.
Kumar et al., "NADP+–specific isocitrate dehydrogenase interaction with metalloporphyrin in rat brain," *Clinical Chemistry and Enzymology Communications* 7(5–6):349–357, 1997.
Sakurai et al., "Model of the Coordination Site for Cobalt–Substituted Cyochrome $P450_{cam}$," *Journal of Inorganic Biochemistry* 26:55–62, 1986.
Takayanagi et al., "The Ligation of Phosphine Derivatives and the Oxygen–binding Properties of the Cobalt Mesoporphyrin IX Dimethyl Ester in Toluene," *Bulletin of the Chemical Society of Japan* 48(10):2618–2622, 1975.
Wicker Jr. et al., "The Relationship Between Enthalpy Changes and Oxygenation Constants for Cobalt and Iron Porphyrins," *Inorganica Chimica Acta.* 78:181–189, 1983.
Yamamoto et al., "Oxygen Binding of Cobalt(II) Proto–, Deutero– and Meso– Porphyrin IX Dimethyl Ester Complexes in Organic Solvents," *Bioinorganic Chemistry* 7:189–201, 1977.

* cited by examiner

*Primary Examiner*—Peter O'Sullivan
(74) *Attorney, Agent, or Firm*—Seed IP Law Group PLLC

(57) ABSTRACT

Cobalt-porphyrin (Co-P) complexes for use as anti-obesity agents, and compositions and methods related thereto. The Co-P complexes exhibit reduced redox activity compared to cobalt mesoporphyrin (Co-MP) and cobalt protoporphyrin (Co-PP), which alleviates the deleterious effects associated with administration of Co-P associated with oxidative stress, particularly in the context of injection site toxicity.

3 Claims, 10 Drawing Sheets

COBALT-PORPHYRIN COMPLEXES AND USE THEREOF AS AN ANTI-OBESITY AGENT

BACKGROUND OF THE INVENTION

1. Field of the Invention

The present invention relates generally to cobalt-porphyrin complexes which are useful as anti-obesity agents, as well as to compounds, compositions and methods related to the same.

2. Description of the Related Art

Porphine i is the parent substance of porphyrins, a group of compounds found in all living matter and which are the basis of respiratory pigments in animals and plants. Porphyrins constitute a class of compounds wherein the hydrogen atoms of porphine's pyrrole rings are substituted with various side chains. Porphyrins have received extensive study, much of which is presented in a multi-volume treatise entitled *The Porphyrins,* D. Dolphin, Ed., Academic Press, N.Y., 1978.

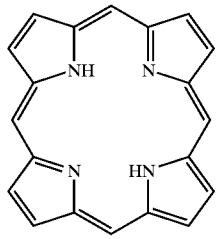

i

An exemplary porphyrin is protoporphyrin IX ii. Protoporphyrin IX is the immediate precursor of heme, which is the complex formed upon chelation of iron by protophorphryin. In addition to iron, protoporphyrin IX readily chelates with other metals. When chelated to cobalt, the resulting complex is cobalt-protoporphyrin iii (including salts and/or ligand complexes thereof).

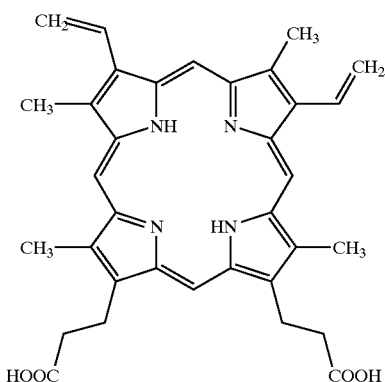

ii

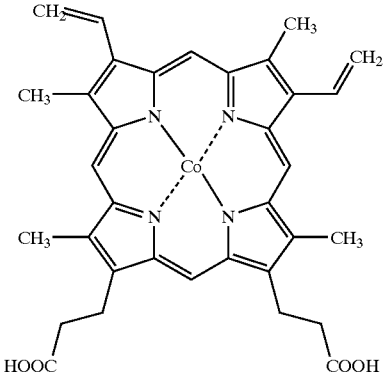

iii

A related analogue of protoporphyrin IX ii is mesoporphyrin iv, which differs from protoporphyrin to the extent that the two ethylene side chains are fully saturated. When chelated to cobalt, cobalt mesoporphyrin v results (including salts and/or ligand complexes thereof).

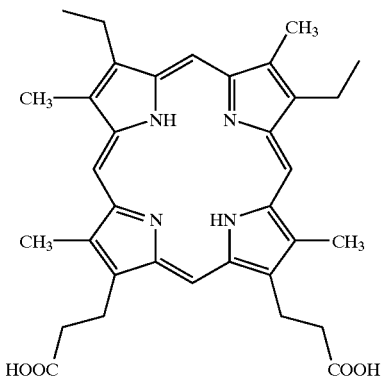

iv

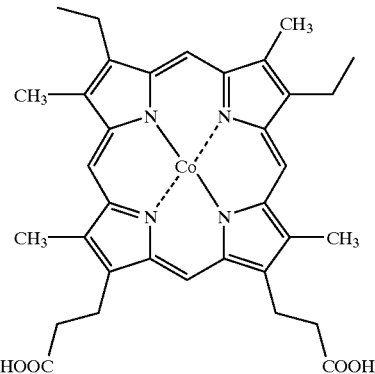

v

Cobalt protoporphyrin ("Co-PP") has been reported to regulate food intake and body weight in rats (Galbraith and Kappas, *Proc. Natl. Acad Sci. U.S.A.* 86:7653–7657, 1989), as well as in other animals such as rats, dogs and monkeys. A single subcutaneous injection of Co-PP produces a prompt dose-dependent decrease in food intake in Sprague Dawley rats. This result is accompanied by a sustained decrease in body weight, that is characterized by decreases in carcass fat content without changes in protein content. Smaller doses of Co-PP delivered by intracerebroventricular administration has also been found to elicit the same effect.

The regulatory effect of Co-PP has also been extended to animals that are genetically destined to become markedly obese. Thus, subcutaneous administration of Co-PP to Zucker rats whose obesity is conferred by homozygosity of the fa gene (fa/fa) produces long-sustained reduction in body weight (Galbraith and Kappas, *Pharmacology* 41:292–298, 1990). The effect of Co-PP is profound and believed to be caused by the phenotype of gene expression in the fa/fa animal to revert to a phenotype similar to that of the heterozygous lean animal. Whereas cobalt mesoporphyrin ("Co-MP") has a comparable biological profile, the same effect is not found upon administration of inorganic cobalt, or a number of other metal chelates of porphyrins. The mechanism of action of Co-PP for regulation of body weight is unknown, and it has been shown that the weight loss in rats is not mediated by the neuropeptide Y system (Choi et al, *Brain Research* 729:223–227, 1996; Turner et al, *Physiology and Behavior* 56:10009–1014, 1994).

Administration of Co-PP and/or Co-MP for regulation of body weight is not without drawbacks. For example, oxidative stress has been associated with administration of high doses of Co-PP (see Tomaro et al., *Arch. Biochem. Biophys.* 286:610–617, 1991). Accordingly, there is a need in the art for compounds which have the beneficial properties associated with Co-PP and/or Co-MP, such as the ability to regulate body weight, but which not possess the unwanted side-effects presently encountered with administration of the same. The present invention fulfills these needs and provides other related advantages.

BRIEF SUMMARY OF THE INVENTION

Briefly stated, the present invention is directed to cobalt-porphyrin (Co-P") complexes which are useful as an anti-obesity agents, as well as to compositions and methods related to the same. Cobalt-porphyrins of this invention are referred to as a "complex" since the porphyrin ring serves as a tetradentate ligand which complexes (i.e., chelates) the central cobalt ion. The Co-P complexes of this invention have activity over a wide range of therapeutic application, including (but not limited to) use as anti-obesity agents.

More specifically, the cobalt-porphyrin (Co-P) complexes of this invention have the following structure (I):

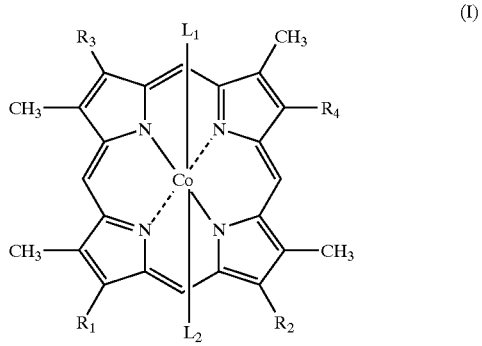

(I)

including salts thereof, wherein:

$R_1$ and $R_2$ are the same or different and independently —$(CH_2)_n$-A-$R_5$, wherein A is —C(=O)O—, —OC(=O)—, —C(=O)N(R)—, —N(R)C(=O)—, —C(=O)—, —N(R)—, —O— or —S—, R is hydrogen, alkyl, substituted alkyl, arylalkyl or substituted arylalkyl, and n is 2 or 3;

$R_3$ and $R_4$ are the same or different and independently —CH=$CH_2$ or —$CH_2CH_3$;

$R_5$ is, at each occurrence, the same or different and independently hydrogen, alkyl, substituted alkyl, aryl, substituted aryl, arylalkyl, substituted arylalkyl, heterocycle, substituted heterocyle, heterocylcealky or substituted heterocyclealkyl; and $L_1$ and $L_2$ are optional ligands;

and with the proviso that the cobalt-porphyrin complex of structure (I) has reduced redox activity compared to cobalt mesoporphyrin.

In one embodiment, reduced redox activity is achieved by conjugating Co-P, at the $R_1$ and/or $R_2$ positions, with a reactive oxygen species (ROS) modulating agent. In an alternative embodiment, reduced redox activity is imparted by coordination of Co-P with an appropriate $L_1$ and/or $L_2$ ligand.

It should be understood that structure (I) above is intended to encompass both cobalt (II) and cobalt (III), as well as any coordination complex thereof. For example, when chelated by the tetradentate porphyrin ligand, cobalt typically has an oxidation number of (II) or (III)—that is, $Co^{+2}$ or $Co^{+3}$, respectively—and has a coordination number of 4 (square planer) or 6 (octahedral). Thus, when in a tetrahedral form, two additional ligands (designated as $L_1$ and $L_2$ in structure (I) above) are coordinated with the cobalt ion. On the other hand, when in the tetrahedral form, $L_1$ and $L_2$ are not present. For this reasons, $L_1$ and $L_2$ are referred to as "optional" in structure (I) above and, when present, may be the same or different.

These and other aspects of the present invention will become evident upon reference to the following detailed description and attached drawings. To that end, various references are set forth herein which describe in more detail certain aspects of this invention, and are each incorporated by reference in their entirety.

DETAILED DESCRIPTION OF THE INVENTION

Figure 1:
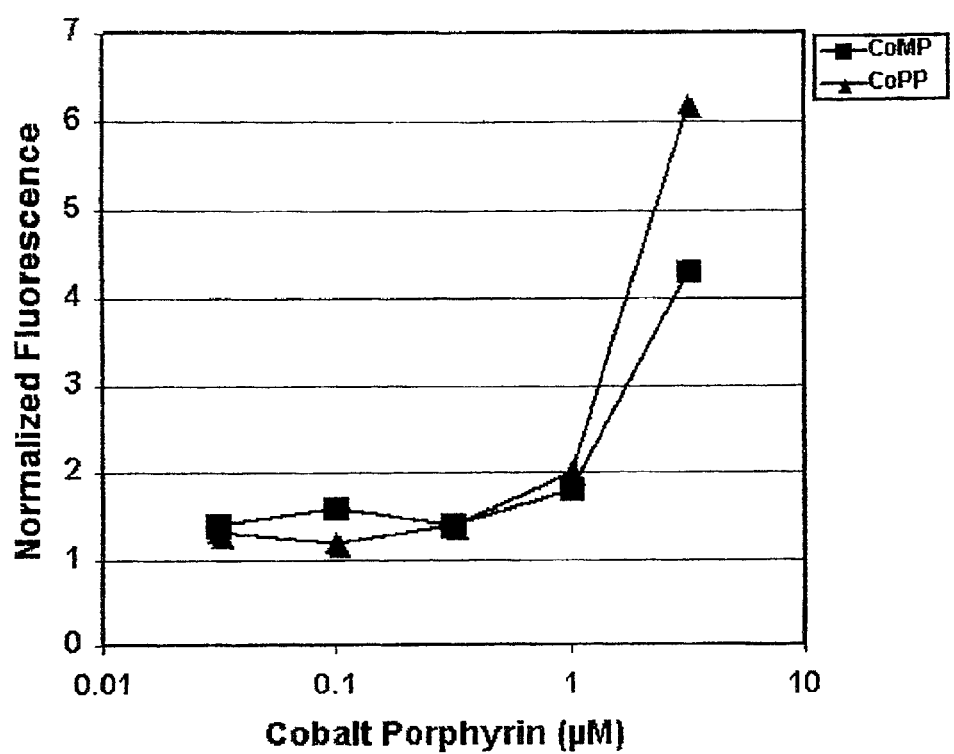
FIG. 1 illustrates reactive oxygen species induced by Co-PP and Co-MP in SH-SY5Y cells.

The present invention is generally directed to cobalt-porphyrin (Co-P) complexes, as well as to compositions and methods related to the same. As noted above, a Co-P complex of this invention has the following structure (I):

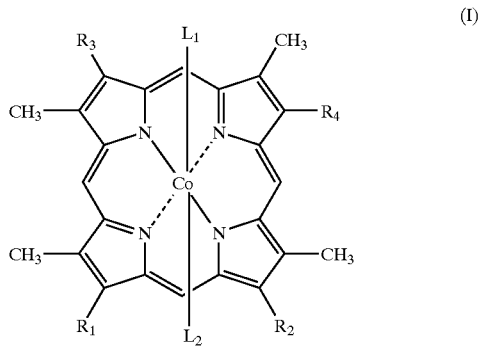

(I)

or a salt thereof, wherein:
R$_1$ and R$_2$ are the same or different and independently —(CH$_2$)$_n$-A-R$_5$, wherein A is —C(=O)O—, —OC(=O)—, —C(=O)N(R)—, —N(R)C(=O)—, —C(=O)—, —N(R)—, —O— or —S—, R is hydrogen, alkyl, substituted alkyl, arylalkyl or substituted arylalkyl, and n is 2 or 3;
R$_3$ and R$_4$ are the same or different and independently —CH=CH$_2$ or —CH$_2$CH$_3$;
R$_5$ is, at each occurrence, the same or different and independently hydrogen, alkyl, substituted alkyl, aryl, substituted aryl, arylalkyl, substituted arylalkyl, heterocycle, substituted heterocyle, heterocylclealky or substituted heterocyclealkyl; and
L$_1$ and L$_2$ are optional ligands;
and with the proviso that the cobalt-porphyrin complex of structure (I) has reduced redox activity compared to cobalt mesoporphyrin (Co-MP).

As used herein, the terms used above have the following meaning:

"Alkyl" means a straight chain or branched, saturated or unsaturated, cyclic or non-cyclic hydrocarbon having from 1 to 10 carbon atoms, while "lower alkyl" has the same meaning but only has from 1 to 6 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Unsaturated alkyls contain at least one double or triple bond between adjacent carbon atoms (also referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1 butynyl, and the like. Representative saturated cyclic alkyls include cyclopropyl, cyclobutyl, cyclopentyl, cyclohexyl, (cyclohexyl)CH$_2$—, and the like; while unsaturated cyclic alkyls include cyclopentenyl and cyclohexenyl, and the like. Cycloalkyls are also referred to herein as "carbocyclic" rings systems, and include bi- and tri-cyclic ring systems having from 8 to 14 carbon atoms such as a cycloalkyl (such as cyclo pentane or cyclohexane) fused to one or more aromatic (such as phenyl) or non-aromatic (such as cyclohexane) carbocyclic rings.

"Halogen" means fluorine, chlorine, bromine or iodine.
"Oxo" means a carbonyl group (i.e., "=O").
"Aryl" means an aromatic carbocyclic moiety such as phenyl or naphthyl.

"Arylalkyl" means an alkyl having at least one alkyl hydrogen atom replaced with an aryl moiety, such as benzyl, —(CH$_2$)$_2$phenyl, —(CH$_2$)$_3$phenyl, —CH(Phenyl)$_2$, and the like.

"Heteroaryl" means an aromatic heterocycle ring of 5- to 10 members and having at least one heteroatom selected from nitrogen, oxygen and sulfur, and containing at least 1 carbon atom, including both mono- and bicyclic ring systems. Representative heteroaryls are pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, and quinazolinyl.

"Heteroarylalkyl" means an alkyl having at least one alkyl hydrogen atom replaced with a heteroaryl moiety, such as —CH$_2$pyridinyl, —CH$_2$pyrimidinyl, and the like.

"Heterocycle" means a 5- to 7-membered monocyclic, or 7- to 10-membered bicyclic, heterocyclic ring which is either saturated, unsaturated, or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include heteroaryls as defined above. Thus, in addition to the heteroaryls listed above, heterocycles also include morpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Heterocyclealkyl" means an alkyl having at least one alkyl hydrogen atom replaced with a heterocycle, such as —CH$_2$morpholinyl, and the like.

The term "substituted" as used herein means any of the above groups (i.e., aryl, arylalkyl, heterocycle and heterocyclealkyl) wherein at least one hydrogen atom is replaced with a substituent. In the case of an oxo substituent ("=O") two hydrogen atoms are replaced. Substituents include halogen, hydroxy, alkyl, substituted alkyl (such as haloalkyl, mono- or di-substituted aminoalkyl, alkyloxyalkyl, and the like), aryl, substituted aryl, arylalkyl, substituted arylalkyl, heterocycle, substituted heterocycle, heterocyclealkyl, substituted heterocyclealkyl, —NR$_a$R$_b$, —NR$_a$C(=O)R$_b$, —NR$_a$C(=O)NR$_a$R$_b$, —NR$_a$C(=O)OR$_b$ —NR$_a$SO$_2$R$_b$, —OR$_a$, —C(=O)R$_a$ —C(=O)OR$_a$ —C(=O)NR$_a$R$_b$, —OC(=O)R$_a$, —OC(=O)OR$_a$, —OC(=O)NR$_a$R$_b$, —NR$_a$SO$_2$R$_b$, or a radical of the formula -Y-Z-R$_a$ where Y is alkanediyl, substitute alkanediyl, or a direct bond, Z is —O—, —S—, —S(=O)—, —S(=O)$_2$—, —N(R$_b$)—, —C(=O)—, —C(=O)O—, —OC(=O)—, —N(R$_b$)C(=O)—, —C(=O)N(R$_b$)— or a direct bond, wherein R$_a$ and R$_b$ are the same or different and independently hydrogen, amino, alkyl, substituted alkyl (including halogenated alkyl), aryl, substituted aryl, arylalkyl, substituted arylalkyl, heterocycle, substituted heterocycle, heterocyleakyl or substituted heterocyclealkyl, or wherein R$_a$ and R$_b$ taken together with the nitrogen atom to which they are attached form a heterocycle or substituted heterocycle.

In one embodiment, both of R$_3$ and R$_4$ are —CH=CH$_2$ and a Co-P complex of this invention has the following structure (II):

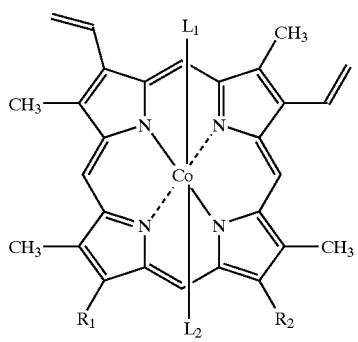

(II)

In another embodiment, both $R_3$ and $R_4$ are —$CH_2CH_3$ and a Co-P complex of this invention has the following structure (III):

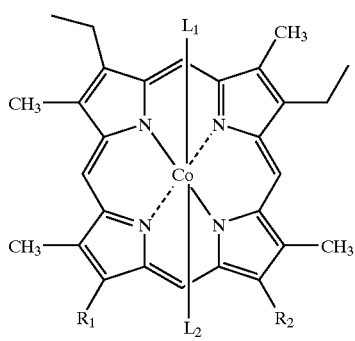

(III)

In still a further embodiment, $R_1$ and $R_2$ are both —$(CH_2)_n$-A-$R_5$ wherein A is —C(=O)O—, and a Co-P complex of this invention has the following structure (IV):

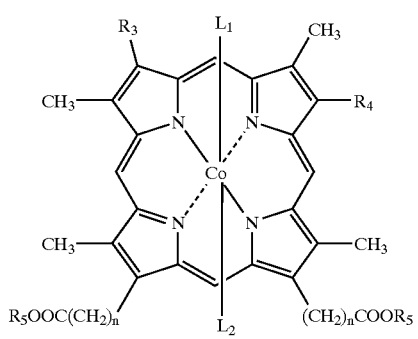

(IV)

In still other embodiments, $R_1$ and $R_2$ are both —$(CH_2)_n$-A-$R_5$ wherein A is —OC(=O)—, —C(=O)N(R)—, —N(R)C(=O)—, —C(=O)—, —N(R)—, —O— or —S—, and a Co-P complex of this invention has the following structure (V), (VI), (VII), (VIII), (IX), (X) or (XI), respectively:

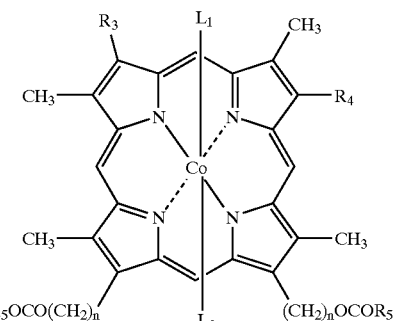

(V)

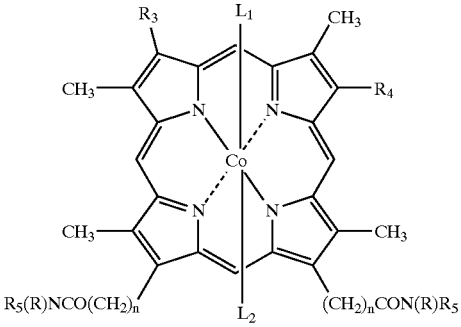

(VI)

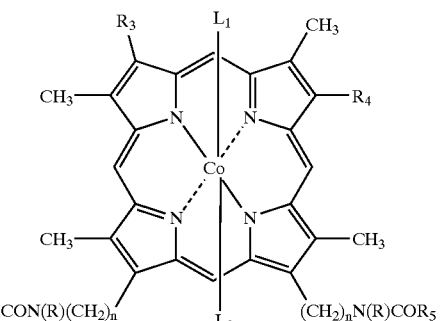

(VII)

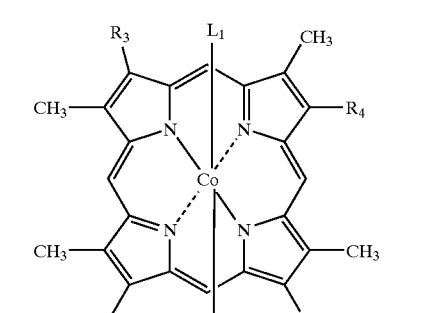

(VIII)

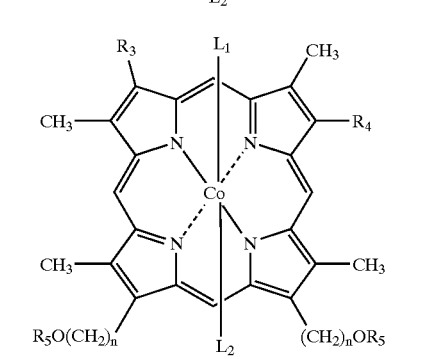

(IX)

-continued (X)

(XI)

In the context of this invention, it has been found that a Co-P complex of structure (I) above retains many of the beneficial properties associated with Co-PP and/or Co-MP, such as the ability to regulate body weight, but reduces and/or eliminates many of the unwanted side-effects presently encountered upon administration of the same. Although not intending to be limited by the following theory, it is believed that administration of Co-PP and/or Co-MP triggers significant production of reactive oxygen species at the site of injection, particularly hydrogen peroxide, which have deleterious consequences to tissue. For example, such reactive oxygen species result in free radical damage to DNA, protein and membrane components, and increased intracellular levels of reactive oxygen species lead to increased vulnerability to apoptotic and necrotic cell death. Indeed, administration of high doses of Co-PP results in induction of heme oxygenase, and such induction is preceded by oxidative stress that is triggered by depletion of reduced glutathione levels (see Tomao et al. *Arch. Biochem. Biophys.* 286:610–617, 1991).

In the practice of this invention, generation of reactive oxygen species is modulated by conjugating Co-P with a reactive oxygen species (ROS) modulating agent, and/or by coordinating Co-P with a ligand. In the first case, one or both of the $R_1/R_2$ moieties serves as a ROS modulating agent. Linking $R_5$ via linker A may be achieved by chemistry known in this field, such as, for example, starting with the corresponding carboxylic acid (i.e., wherein A is —C(=O) O— and $R_5$ is hydrogen). In the second case, Co-P is complexed with one or more ligands, $L_1$ and $L_2$. Again, formation of such complexes is know to one skilled in this field, and is accomplished by appropriate selection and coordination of the $L_1$ and/or $L_2$ ligands. As used herein, a "ROS modulating agent" means a moiety which can be covalently joined to Co-P (through linker A), and which serves to modulate generation of ROS normally induced by administration of Co-PP and/or Co-MP. In this regard, a "ligand" means any molecule or ion that has at least one electron pair that can be donated. In general, the ability of such a moiety or ligand to modulate generation of ROS can be identified by its ability, when bound to Co-P of structure (I), to prevent generation of reactive oxygen species in the assays disclosed in Examples 15 and/or 16.

In one embodiment of this invention, the ROS modulating agent is thioctic acid or ebelsen, as depicted below, joined to Co-P via linker A of structure (I):

Thioctic Acid

Ebselen

Thioctic acid is a cyclic disulfide that is interconvertible with dihydrothioctic acid. Ebelsen is a selenoorganic compound that is an effective mimic of glutathione peroxidase, an enzyme that catalyses the reduction of hydroperoxides at the expense of thiol reducing equivalents (Sies, H, *Free Radical Biology & Medicine* 14:313–323, 1993). The substrate specificity of ebselen ranges from hydrogen peroxide to smaller organic hydroperoxides to membrane-bound phospholipids and cholesterol hydroperoxides. Both thioctic acid and ebelsen are endogenous cofactors of mitochondrial pyruvate dihydrogenase and α-ketoglutarate dehydrogenase complexes, help maintain glutathione and α-tocopherol in their reduced states, and possess intrinsic free-radical scavenging properties.

In generally, ROS modulating agents may be joined to Co-P by formation of a suitable covalent bond. For example, if an amide bond is to be utilized, the carboxylic acid of thioctic acid may be converted to the corresponding amide by well-known organic chemistry techniques, or an amine-substituted derivative of ebelsen may be utilized. The amine may then be reacted with the carboxylic acid of Co-PP (or Co-MP), again using well-known techniques, to yield representative compounds (Va) and (Vb). (Note: In the following structures (Va) and (Vb) optional ligands $L_1$ and $L_2$ are not depicted):

(Va)

-continued

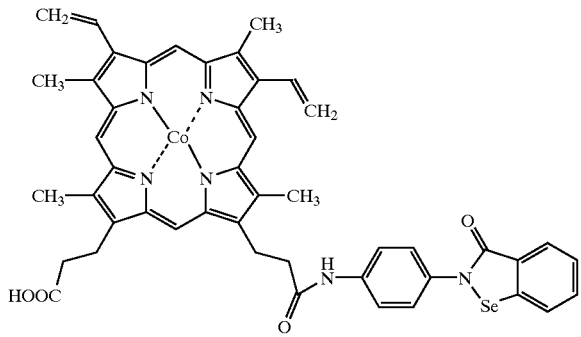

(Vb)

In another embodiment, an as mentioned above, the generation of ROS are modulated by coordinating Co-P with a ligand. Formation of such complexes is generally known to one skilled in this field, and is accomplished by appropriate selection and coordination of the $L_1$ and/or $L_2$ ligands. In this regard, suitable ligands include any ligand capable of donating electrons to the electron-deficient metal ion, which, in this case, is cobalt. Such ligands are capable of occupying one position in the inner coordination sphere and forming at least one coordinate bond to cobalt, and are typically unidentate ligands. Representative ligands include, but are not limited to, halo (fluoro, chloro, bromo or iodo), cyano, amino, mono- or di-substituted amino wherein the substituent(s) is(are) as defined above for $R_a$ and $R_b$, amino groups of amino acid such as glycinate, and substituted or unsubstituted heterocycles containing one or more nitrogen, oxygen and/or sulfur heteroatoms as defined above, including substituted or unsubstituted heteroaryls such as piperidine and imidazole.

As noted above, Co-P compounds of structure (I) must have reduced redox activity compared to cobalt mesoporphyrin (Co-MP). Such activity can be readily determined by, for example, the assay disclosed in Example 16. In that assay, redox activity is measured by oxygen consumption catalyzed by a Co-P test compound in the presence of ascorbate and TMPD. This same assay is also performed on Co-MP, and a comparison is made to determine whether the test compound exhibits reduced redox activity compared to Co-MP.

In the context of novel Co-P complexes of this invention, the Co-P complex of structure (I) has reduced redox activity compared to Co-MP. Such comparison is made by assigning a value of 100% to the redox activity of Co-MP. A novel Co-P complex of this invention has 5% (or less) the redox activity of Co-MP. Preferably, the Co-P complex has a redox activity of 4% (or less), more preferably of 3% (or less), even more preferably of 2% (or less), and most preferably of 1% (or less) the redox activity of Co-MP. In even a more specific and preferred embodiment, the redox activity of the novel Co-P complex of this invention is not detectable by the assay disclosed in Example 16 (i.e., 0% the redox activity of Co-MP).

In the context of the methods of this invention, such as methods for treating obesity, the Co-P complex of structure (I) has 50% (or less) the redox activity of Co-MP. Preferably, the Co-P complex has 20% (or less), more preferably 10% (or less), even more preferably of 5% (or less), and most preferably of 1% (or less) the redox activity of Co-MP. In even a more specific and preferred embodiment, the redox activity of the Co-P complex administered to a patient within a method of this invention is not detectable by the assay disclosed in Example 16.

Such redox activity measurements are illustrated in Table 3 of Example 18, wherein Co-MP was assigned a value of 1 (i.e., 100%). In that example, Co-PP was found to have a higher redox activity than Co-MP (2.2 times higher), while the representative Co-P complexes identified in Table 3 all had reduced redox activity (with some having no detectible activity) compared to Co-MP.

A Co-P complex of this invention, or a pharmaceutically acceptable salt thereof, is administered to a patient in a therapeutically effective amount. A therapeutically effective amount is an amount calculated to achieve the desired effect. It will be apparent to one skilled in the art that the route of administration may vary with the particular treatment. Routes of administration may be either non-invasive or invasive. Non-invasive routes of administration include oral, buccal/sublingual, rectal, nasal, topical (including transdermal and ophthalmic), vaginal, intravesical, and pulmonary. Invasive routes of administration include intraarterial, intravenous, intradermal, intramuscular, subcutaneous, intraperitoneal, intrathecal and intraocular. In a typical embodiment, administration is by injection.

The required dosage may vary with the particular treatment and route of administration. In general, dosages for Co-P complex will be from about 1 to about 5 milligrams of the compound per kilogram of the body weight of the host animal per day; frequently it will be between about 100 μg and about 5 mg but may vary up to about 50 mg of compound per kg of body weight per day. Therapeutic administration is generally performed under the guidance of a physician, and pharmaceutical compositions contain the mitochondria protecting agent in a pharmaceutically acceptable carrier. These carriers are well known in the art and typically contain non-toxic salts and buffers. Such carriers may comprise buffers like physiologically-buffered saline, phosphate-buffered saline, carbohydrates such as glucose, mannose, sucrose, mannitol or dextrans, amino acids such as glycine, antioxidants, chelating agents such as EDTA or glutathione, adjuvants and preservatives. Acceptable non-toxic salts include acid addition salts or metal complexes, e.g., with zinc, iron, calcium, barium, magnesium, aluminum or the like (which are considered as addition salts for purposes of this application). Illustrative of such acid addition salts are hydrochloride, hydrobromide, sulphate, phosphate, tannate, oxalate, fumarate, gluconate, alginate, maleate, acetate, citrate, benzoate, succinate, malate, ascorbate, tartrate and the like. If the active ingredient is to be administered in tablet form, the tablet may contain a binder, such as tragacanth, cornstarch or gelatin; a disintegrating agent, such as alginic acid; and a lubricant, such as magnesium stearate. If administration in liquid form is desired, sweetening and/or flavoring may be used, and intravenous administration in isotonic saline, phosphate buffer solutions or the like may be effected.

The following examples are offered by way of illustration, and not by way of limitation.

EXAMPLES

Example 1

Acidic Esterification of Cobalt (III) Mesoporphyrin IX

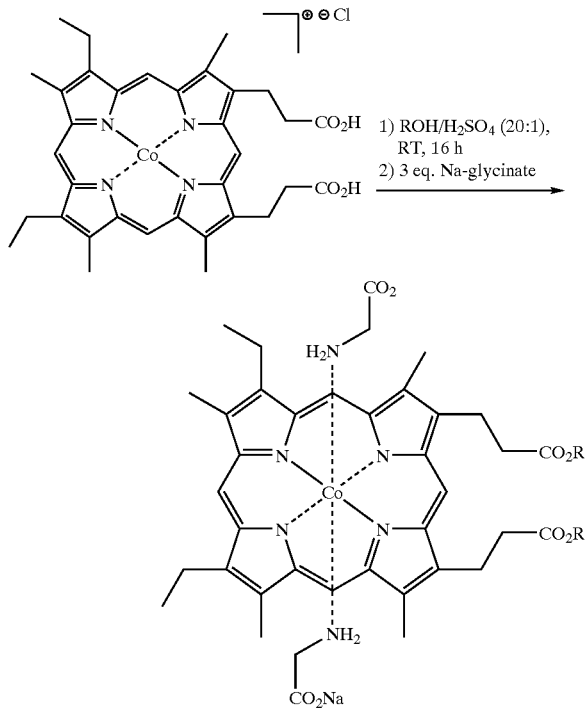

Cobalt (III) mesoporphyrin IX, chloride salt (Porphyrin Products, Inc., Logan, Utah) (329.5 mg, 0.500 mmol) was slurried in dry alcohol (10 mL). The mixture was cooled on an ice-bath and while stirred, $H_2SO_4$ (0.500 ml) was added dropwise over ca 30 sec. The reaction flask was tightly stoppered and the mixture was stirred overnight (ca 16 h) at ambient temperature. The reaction mixture was partitioned between $CH_2Cl_2$ (40 ml) and 1.0 M HCl (20 ml), the organic layer was dried over anhydrous $Na_2SO_4$. The solvent was removed by rotary evaporation to provide a deep red glassy material. Further purification was achieved by silica gel flash chromatography using $CH_2Cl_2$/MeOH (9/1 and 85/15) as eluents. Appropriate fractions were pooled and evaporated, furnishing the desired diester as its putative chloride salt.

Conversion to the respective bisglycinate complexes was performed as follows. The putative chloride salt was dissolved in EtOH at a concentration of 10 mM. To this solution was added a methanolic solution of sodium glycinate (0.10 M, 3.0 eq.). After 10 min of stirring, the reaction solution was evaporated to dryness and redissolved in dioxane:$H_2O$ (2:3, 25 ml), frozen, and lyophilized to a fluffy red solid. $^1$H-NMR spectroscopy confirmed the presence of axially coordinated glycinate ligands and the presence of close to one equivalent of un-coordinated sodium glycinate. High resolution MALDI-FTMS analysis provided composition data for the un-coordinated cobalt mesoporphyrin diesters.

By the above procedures, the following compounds were made and characterized:

(1-1) Cobalt (III) Mesoporphyrin IX Bisglycinate Monosodium Salt, Dimethyl Ester Yield: 84%; $^1$H-NMR. ($d_3$-MeOD): 10.56 (s, 1H), 10.52 (s, 1H), 10.50 (s, 1H), 10.49 (s, 1H), 4.55 (t, 3H), 4.24 (m, 4H), 3.79–3.77 (4s, 12H), 3.62 (s, 6H), 3.40 (m, 4H), 1.96 (m, 6H), −4.08 (m, 4H), −5.45 (m, exchangeable); MALDI-FTMS: calc. for $C_{36}H_{40}CoN_4O_4^+$—651.2376. found—651.2355.

(1-2) Cobalt (III) Mesoporphyrin IX Bisglycinate Monosodium Salt, Dibutyl Ester

Yield: 87%; $^1$H-NMR ($d_3$-MeOD): 10.58 (s, 1H), 10.52 (s, 1H), 10.50 (s, 1H), 10.49 (s, 1H), 4.55 (t, 3H), 4.24 (m, 4H), 4.14 (m, 4H) 3.79–3.77 (4s, 12H), 3.40 (m, 4H), 1.96 (m, 6H), 1.59 (m, 4H), 1.36 (m, 4H), 0.90 (m, 6H), −4.08 (m, 4H), −5.46 (m, exchangeable); MALDI-FTMS: calc. for $C_{42}H_{52}CoN_4O_4^+$—735.3315. found—735.3285.

(1-3) Cobalt (III) Mesoporphyrin IX Bisglycinate Monosodium Salt, Diisobutyl Ester Yield: 86%; $^1$H-NMR ($d_3$-MeOD): 10.59 (s, 1H), 10.52 (s, 1H), 10.50 (s, 1H), 10.49 (s, 1H), 4.55 (t, 3H), 4.24 (m, 4H), 3.95 (m, 4H), 3.81–3.76 (4s, 12H), 3.42 (m, 4H), 1.96 (m, 6H), 1.93 (m, 2H), 0.96–0.86 (m, 12H), −4.08 (m, 4H), −5.47 (m, exchangeable); MALDI-FTMS: calc. for $C_{42}H_{52}CoN_4O_4^+$—735.3315. found—735.3300.

(1-4) Cobalt (III) Mesoporphyrin IX Bisglycinate Monosodium Salt, Diisoamyl Ester Yield: 91%; $^1$H-NMR ($d_3$-MeOD): 10.57 (s, 1H), 10.52 (s, 1H), 10.49 (s, 1H), 10.48 (s, 1H), 4.54 (t, 3H), 4.23 (m, 4H), 4.18 (t, 2H), 4.03 (t, 2H), 3.79–3.76 (4s, 12H), 3.39 (m, 4H), 1.96 (m, 6H), 1.69 (m, 2H), 1.52 (m, 4H), 0.94–0.89 (m, 12H), −4.09 (m, 4H), −5.47 (m, exchangeable); MALDI-FTMS: calc. for $C_{44}H_{56}CoN_4O_4^+$— 763.3628. found—763.3651.

(1-5) Cobalt (III) Mesoporphyrin IX Bisglycinate Monosodium Salt, Diethyl Ester

Yield: 86%; $^1$H-NMR ($d_3$-MeOD): 10.58 (s, 1H), 10.52 (s, 1H), 10.50 (s, 1H), 10.49 (s, 1H), 4.55 (t, 3H), 4.24 (m, 4H), 4.15 (m, 4H), 3.79–3.77 (4s, 12H), 3.40 (m, 4H), 1.96 (m, 6H), 1.18 (m, 4H), −4.09 (m, 4H), −5.46 (m, exchangeable); MALDI-FTMS: calc. for $C_{38}H_{44}CoN_4O_4^+$—679.2689. found—679.2678.

(1-6) Cobalt (III) Mesoporphyrin IX Bisglycinate Monosodium Salt, Diisopropyl Ester Yield: 66%; $^1$H-NMR ($d_3$-MeOD): 10.59 (s, 1H), 10.52 (s, 1H), 10.50 (s, 1H), 10.49 (s, 1H), 5.08 (m, 2H), 4.54 (t, 3H), 4.24 (m, 4H), 3.79–3.77 (4s, 12H), 3.37 (m, 4H), 1.96 (m, 6H), 1.16 (m, 12H), −4.09 (m, 4H), −5.48 (m, exchangeable); MALDI-FTMS: calc. for $C_{40}H_{48}CoN_4O_4^+$—707.3002. found—707.2995.

Example 2

CDMI Mediated Formation of Cobalt (III) Mesoporphyrin IX Dimethyl Ester

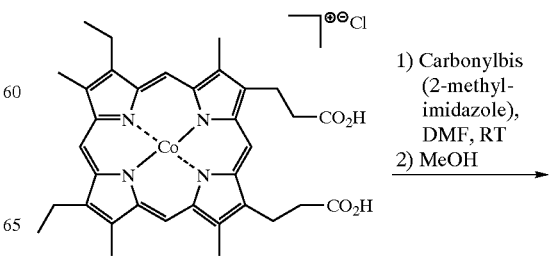

-continued

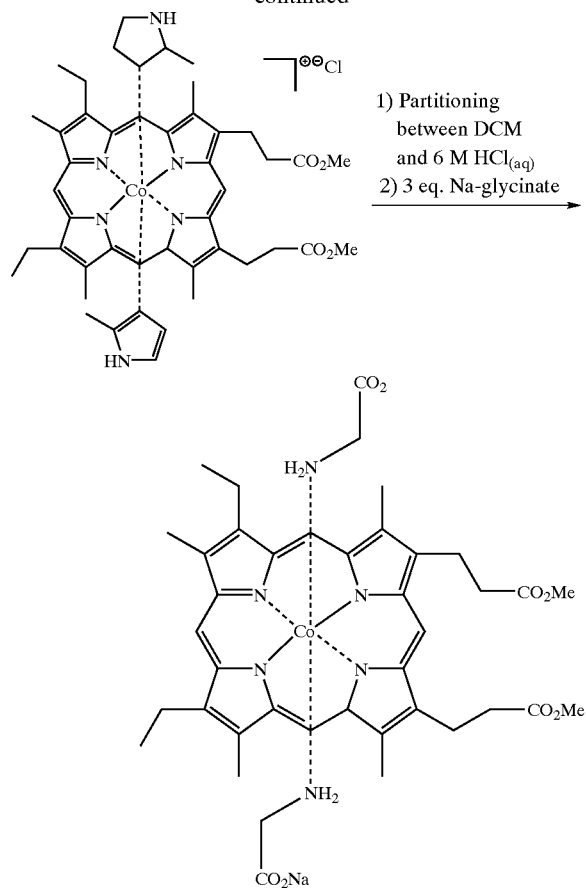

Cobalt (III) mesoporphyrin IX, chloride salt (Porphyrin Products, Inc., Logan, Utah) (329.5 mg, 0.500 mmol) was dried by evaporation of its solution in anhydrous DMF (10 ml). The residue was dissolved in dry DMF (25 ml). Carbonylbis(2-methylimdazole) (380 mg, 2.00 mmol) was added in one portion, the flask stoppered and the contents stirred at ambient temperature for 60 min. Dry methanol (0.405 ml, 10.0 mmol) was added and stirring continued for 3 h. The DMF was removed by rotary evaporation and the residue thus formed further purified by silica gel flash chromatography using $CH_2Cl_2$/MeOH (9/1 and 85/15) as eluents. Appropriate fractions were pooled and evaporated, furnishing 332 mg of the desired dimethyl ester as its putative chloride salt.

Removal of the axial nitrogenous ligands was accomplished by partitioning the crude bis(2-methylimidazole) complex between $CH_2Cl_2$ (40 ml) and 6 M HCl (20 ml). The organic layer was dried over $Na_2SO_4$ and evaporated to give 139 mg of the putatively uncomplexed dimethyl ester.

This material was dissolved in EtOH (20.2 ml) and the resulting solution treated with a methanolic solution of sodium glycinate (0.10 M, 6.1 ml, 3.0 eq.). After 10 min stirring the reaction solution was evaporated to dryness and redissolved in dioxane:$H_2O$ (2:3, 25 ml), frozen, and lyophilized to give a powdery red solid, 203 mg (41%). $^1$H-NMR data was in essence identical to the data obtained for material prepared via direct acidic esterification and confirmed the presence of axially coordinated glycinate ligands and the presence of close to one equivalent of un-coordinated sodium glycinate.

Example 3

Acidic Esterification of Cobalt (III) Protoporphyrin IX

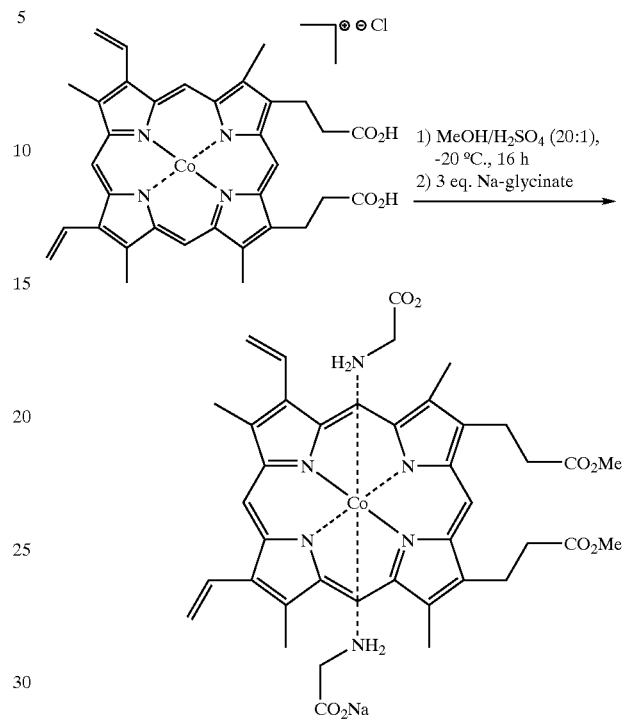

Cobalt (III) protoporphyrin IX, chloride salt (Porphyrin Products, Inc., Logan, Utah) (327.5 mg, 0.500 mmol) was slurried in dry methanol (10 ml). The mixture was cooled on an EtOH/dry ice cooling bath and while stirred, $H_2SO_4$ (0.500 ml) was added dropwise over ca 30 sec. The reaction flask was tightly stoppered and the mixture placed in a freezer kept at −20° C. During the first hour of reaction, the contents of the flask were shaken periodically to avoid deposition of starting material. After being kept cold overnight (ca 16 h), the reaction mixture was partitioned between $CH_2Cl_2$ (40 ml) and 1.0 M HCl (20 ml). The organic layer was dried over anhydrous $Na_2SO_4$, and solvent removed by rotary evaporation. The crude product was further purified by flash silica gel chromatography using $CH_2Cl_2$/MeOH (9/1 and 85/15) as eluents. Appropriate fractions were pooled and evaporated, furnishing the desired dimethyl ester as its putative chloride salt, 257 mg.

This material was dissolved in EtOH (37.6 ml) and the resulting solution treated with a methanolic solution of sodium glycinate (0.10 M, 11.3 ml, 3.0 eq.). After 10 min of stirring, the reaction solution was evaporated to dryness and redissolved in dioxane:$H_2O$ (2:3, 25 ml), frozen, and lyophilized to give a powdery red solid. $^1$H-NMR spectroscopy confirmed the presence of axially coordinated glycinate ligands and the presence of close to one equivalent of uncoordinated sodium glycinate. High resolution MALDI-FTMS analysis provided composition data for the un-coordinated cobalt protopoporphyrin dimethyl ester.

By the above procedures, the following compound was made and characterized:

(3-1) Cobalt (III) Protoporphyrin IX Bisglycinate Monosodium Salt, Dimethyl Ester Yield: 72%; $^1$H-NMR (d3-MeOD): 10.66 (s, 1H), 10.59 (s, 1H), 10.57 (s, 1H), 10.54 (s, 1H), 8.52 (m, 2H), 6.42 (dd, 2H), 6.26 (dd, 2H), 4.53 (t, 3H), 3.87 (s, 3H), 3.85 (s, 3H), 3.79 (s, 3H), 3.76 (s, 3H), 3.65 (s, 3H), 3.59 (s, 3H), 3.40 (m, 4H), −4.00 (m, 4H), −5.22 (m, exchangeable); MALDI-FTMS: calc. for $C_{36}H_{36}CoN_4O_4^+$—647.2068. found—647.2055.

Example 4

CDI-Mediated Syntheses of Dibenzyl Amides of Cobalt(III) Mesoporphyrin IX

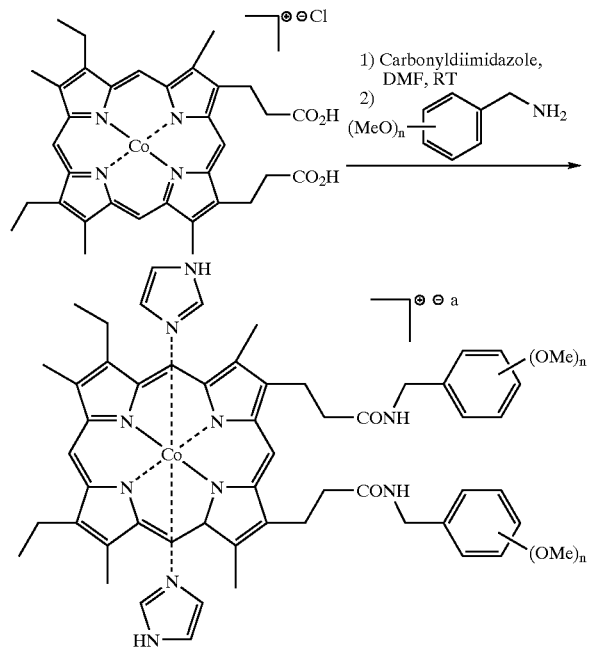

Cobalt (III) mesoporphyrin IX, chloride salt (Porphyrin Products, Inc., Logan, Utah) (33.0 mg, 50 μmol) was dissolved in dry DMF (2.5 ml). To the dark red solution was added 1,1'-carbonyldiimidazole (32.4 mg, 200 μmol) and the reaction mixture stirred at ambient temperature for 30 min. Benzylamine (27.3 μl, 250 μmol) was added to the reaction mixture and stirring was continued for 16 hr with exclusion of moisture and light. Water (100 μl) was added to hydrolyze excess reagents and the solvent was removed by rotary evaporation. The resulting dark red residue was purified by silica gel flash chromatography using portions of $CH_2Cl_2$:MeOH (90/10 and 85/15, respectively) to elute the corresponding diamide of Co-MP IX. Appropriate fractions were pooled, evaporated and dried to furnish a dark red solid. $^1$H-NMR analysis of the crude target molecule revealed the presence of free as well as coordinated imidazole. In a post-synthetic step aimed at removing excess imidazole, a solution of the crude target molecule in $CH_2Cl_2$ (20 ml) was washed with 1/2-saturated NaCl(aq):1 M HCl (aq) (21 ml, 20:1). The organic layer was slowly filtered through a pad of $Na_2SO_4$ and evaporated to afford the bis amide derivative as a red solid. $^1$H-NMR spectroscopy confirmed the presence of axially coordinated imidazole ligands. Yields are based on the molecular weights of the corresponding chloride salt. High resolution MALDI-FTMS analysis provided composition data for the uncoordinated cobalt mesoporphyrin diamides.

By the above procedures, the following compounds were made and characterized:

(4-1) Cobalt (III) Mesoporphyrin IX Bisimidazole Dibenzyl Amide

Yield: 51%; $^1$H-NMR ($d_3$-MeOD): 10.43 (s, 1H), 10.28 (s, 1H), 10.17 (s, 1H), 10.13 (s, 1H), 9.23 (b, 2H), 8.34 (m, 2H), 6.54 (t, 1H), 6.41 (t, 1H), 5.99 (d, 2H), 5.91 (m, 4H), 5.77 (t, 2H), 4.24 (q, 2H), 4.18 (q, 2H), 4.07 (s, 2H), 4.05 (m, 2H), 3.96 (m, 2H), 3.81 (s, 3H), 3.80 (m, 4H), 3.74 (s, 3H), ), 3.06 (m, 4H), 3.06 (s, 3H), 3.01 (s, 3H), 1.99 (t, 3H), 1.95 (t, 3H), 0.60 (s, 2H), −0.22 (s, 2H); MALDI-FTMS: calc. for $C_{48}H_{50}CoN_6O_2^+$— 801.3322. found—801.3345.

(4-2) Cobalt (III) Mesoporphyrin IX Bisimidazole, di(4-methoxybenzyl) amide

Yield: 27%; $^1$H-NMR ($d_3$-MeOD): 10.43 (s, 1H), 10.29 (s, 1H), 10.20 (s, 1H), 10.18 (s, 1H), 9.11 (b, 2H), 8.21 (m, 2H), 5.85 (d, 2H), 5.82 (d, 2H), 5.21 (d, 2H), 5.18 (d, 2H), 4.22 (q, 2H), 4.16 (q, 2H), 4.09 (m, 2H), 4.02 (m, 2H), 4.02 (s, 2H), 3.76 (s, 3H), 3.73 (m, 4H), 3.72 (s, 3H), 3.16 (s, 3H), 3.13 (s, 3H), 3.07 (m, 4H), 3.03 (s, 3H), 2.99 (s, 3H), 1.96 (m, 6H), 0.49 (s, 2H), −0.28 (s, 2H); MALDI-FTMS: calc. for $C_{50}H_{54}CoN_6O_4^+$— 861.3533. found—861.3559.

(4-3) Cobalt (III) Mesoporphyrin IX Bisimidazole bis(3,4-dimethoxybenzyl) amide

Yield: 40%; $^1$H-NMR ($d_3$-MeOD): 10.49 (s, 1H), 10.36 (s, 1H), 10.24 (s, 1H), 10.24 (s, 1H), 9.16 (b, 2H), 8.36 (m, 2H), 5.94 (s, 1H), 5.92 (s, 1H), 5.19 (d, 1H), 5.08 (d, 1H), 4.44 (d, 1H), 4.25 (q, 2H), 4.19 (q, 2H), 4.11 (s, 2H), 4.07 (m, 2H), 4.00 (m, 2H), 3.81 (s, 3H), 3.79 (m, 4H), 3.76 (s, 3H), 3.14 (m, 4H), 3.12 (s, 3H), 3.11 (s, 3H), 3.07 (s, 3H), 3.03 (s, 3H), 2.92 (s, 3H), 2.91 (s, 3H), 1.99 (t, 6H), 0.61 (s, 2H), −0.23 (s, 2H); MALDI-FTMS: calc. for $C_{52}H_{58}CoN_6O_6^+$—921.3744. found—921.3749.

(4-4) Cobalt (III) Mesoporphyrin IX Bisglycinate, di—(N-isopropyl)amide

To a solution of cobalt (III) mesoporphyrin IX, chloride salt (Porphyrin Products, Inc., Logan, Utah) (659 mg, 1.0 mmole) in anhydrous DMF (25 ml) was added carbonyldimethylimidazole (CDMI) (761 mg, 4.0 mmole). The mixture was stirred at room temperature for 1 hour followed by addition of isopropylamine (0.043 ml, 5.0 mmole). The mixture was stirred at room temperature for 17 hours. The reaction was quenched with water (1.0 ml). The solvent was removed under vacuum and the residue was filtrated through a silica gel pluge using DCM/MeOH (90/10) then DCM/MeOH (85/15) as eluents to give the cobalt (III) mesoporphyrin IX bis(methylimidazole), di-(N-isopropyl)amide as a red solid (510 mg). This red solid was dissolved in DCM (40 ml) washed with 6 N aqueous HCl (2×40 ml) and dried over anhydrous sodium sulfate to furnish the cobalt (III) mesoporphyrin IX chloride salt, di-(N-isopropyl)amide as a red solid (80 mg). This material was dissolved in ethanol (11 ml) and treated with a solution of sodium glycinate in methanol (0.10 M×3.24 ml) for 30 minutes. The solvent was removed under vacuum and the residue was lyophilized from water/dioxane (2/3, 15 ml) to give the title compound as a red powder (116 mg). $^1$H NMR (500 MHz, $CD_3OD$) d 10.57(s, 1H), 10.51(s, 1H), 10.50(s, 1H), 10.49(s, 1H), 4.56(m, 2H), 4.24(m, 6H), 3.99(m, 4H), 3.77(s, 12H), 3.17(m, 4H), 1.95 (m, 6H), 0.80(s, 12H), −4.05(m, 4H), −5.51(m, 4H).

Example 5

Synthesis of Cobalt (III) Mesoporphyrin IX Dimethyl Ester (5-1)

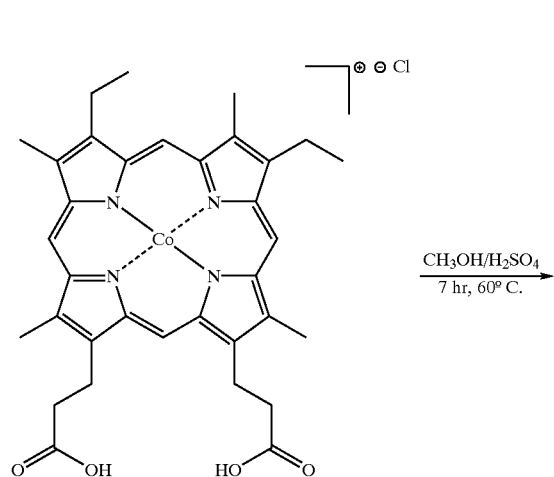

(5-1)

Cobalt (III) mesoporphyrin IX, chloride salt (Porphyrin Products, Inc., Logan, Utah) (0.25 g, 0.37 mmol) was dissolved in anhydrous methanol (6 ml), sulphuric acid (100 μL) and the homogeneous mixture was heated at 60° C. After 7 hrs, methanol was removed under vacuum and the residue was diluted with ethyl acetate (20 ml). The organic layer was washed with water (20 ml×1), brine (20 ml×1), dried over $Na_2SO_4$ and concentrated. The crude product (5-1) was obtained as a red solid (0.26 g, 98% yield and >90% purity by LCMS). LCMS. Calc'd for $C_{36}H_{40}ClCoN_4O_4$: 686. found 651 [M-Cl]$^+$.

Example 6

Synthesis of Cobalt (III) Mesoporphyrin IX Diol (6-1)

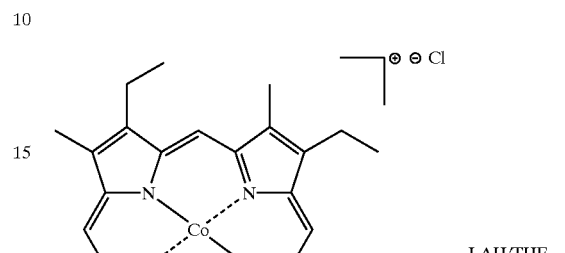

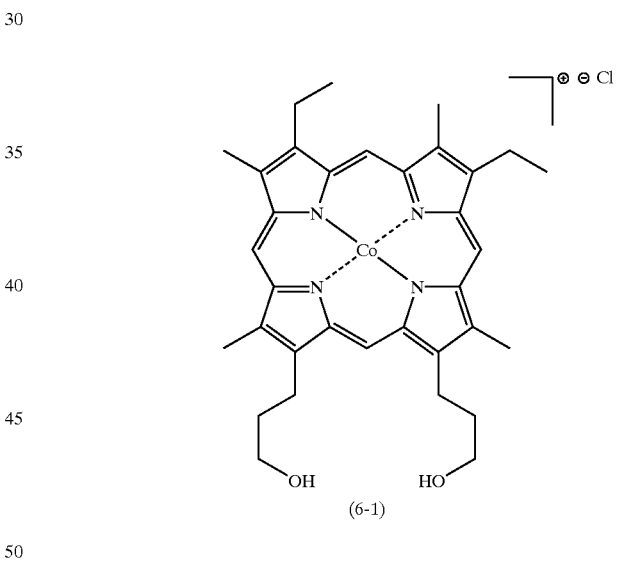

(6-1)

Cobalt (III) mesoporphyrin IX dimethylester, chloride salt (Porphyrin Products, Inc., Logan, Utah) (0.15 g, 0.22 mmol) was dissolved in dry THF (4 ml) under argon atmosphere and cooled to 0° C. Lithium aluminum hydride (0.017 g, 0.43 mmol) was added and heated at 60° C. After 4 hrs, the reaction mixture was cooled to 0° C., quenched with aq. $NH_4Cl$ solution and stirred for 15 min. The solid was removed by filtration over celite and the residue was washed with ethyl acetate. The organic layer was separated, washed with brine (20 ml×1), dried over $Na_2SO_4$ and concentrated. The crude product (6-1) was obtained as a red solid (0.13 g, 100% yield and >85% purity by LCMS). LCMS. Calc'd for $C_{34}H_{40}ClCoN_4O_2$: 630. found 595 [M-Cl]$^+$.

Example 7

Synthesis of Cobalt (III) Mesoporphyrin IX Diacetate (7-1)

Example 8

Synthesis of Cobalt (III) Mesoporphyrin IX Dibenzyl Ester (8-1)

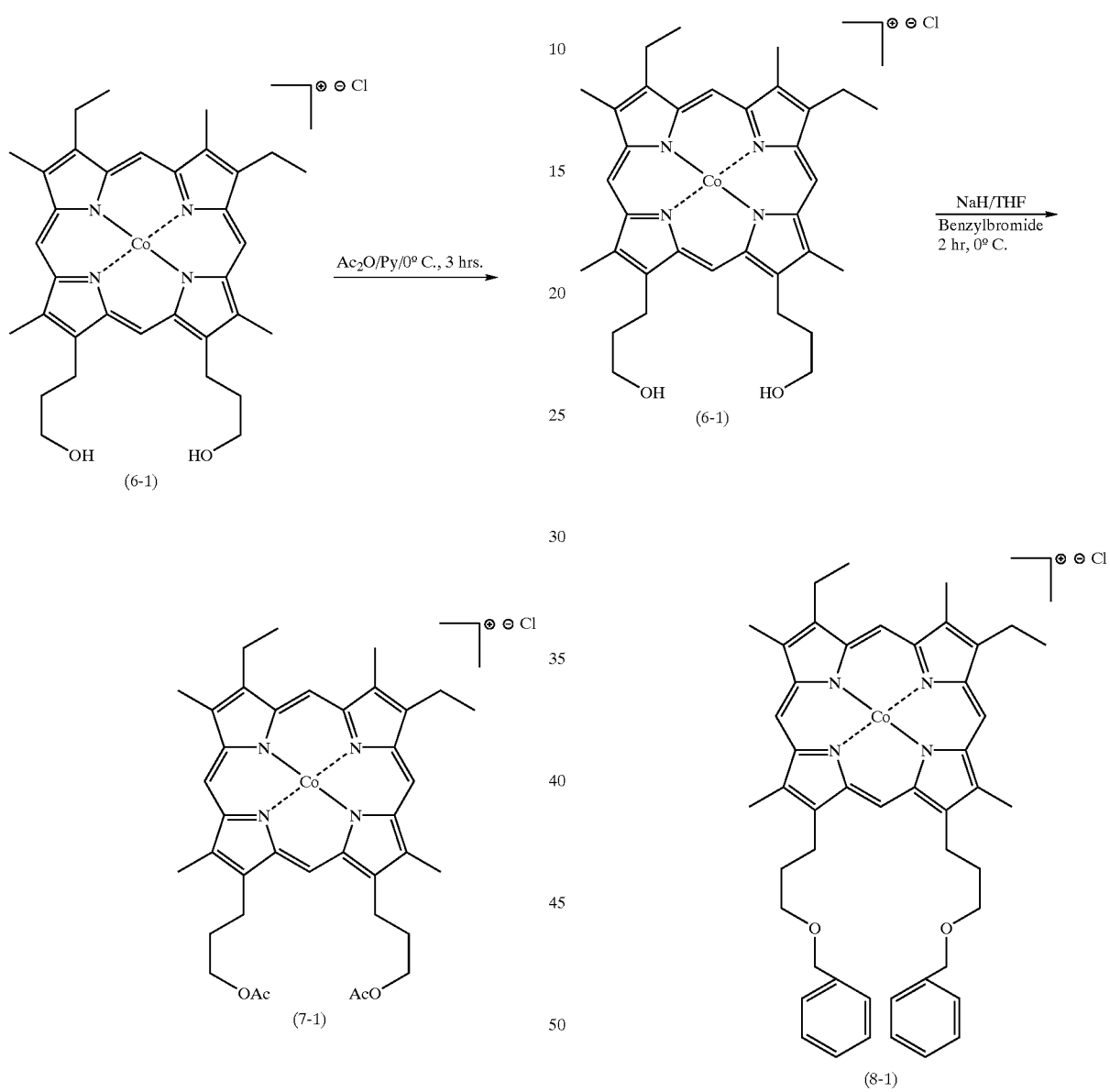

Cobalt mesoporphyrin diol (6-1) (0.025 g, 0.04 mmol) was dissolved in dry $CH_2Cl_2$ (2 ml) under argon atmosphere, cooled to 0° C., pyridine (52 μL, 0.63 mmol) and acetic anhydride (33 μL, 0.32 mmol) were added. The mixture was stirred at 0° C. for 3 hrs. The reaction was quenched with water (20 ml) and diluted with $CH_2Cl_2$ (10 ml). The organic layer was separated, washed with brine (25 ml×1), dried over $Na_2SO_4$, concentrated and dried. The crude product (7-1) was obtained as a red solid (0.028 g, 100% yield, >95% purity by LCMS). LCMS. Calc'd for $C_{38}H_{44}ClCoN_4O_4$: 714. found 679 [M-Cl]$^+$.

To a suspension of sodium hydride (0.006 g, 0.25 mmol) in dry THF (2 ml) at 0° C. under argon atmosphere was added dropwise a solution of cobalt mesoporphyrin diol (6-1) (0.04 g, 0.064 mmol) in THF (0.5 ml). After 30 min, a solution of benzyl bromide (15 μL) in dry THF (0.5 ml) was added and the mixture was stirred at 0° C. for 2 hrs. The reaction was quenched with water (20 ml) and diluted with ethyl acetate (30 ml). The organic layer was separated and washed with water (30 ml×1), brine (30 ml×1), dried over $Na_2SO_4$ and concentrated. The crude product (8-1) was obtained as a red solid (0.053 g). LCMS. Calc'd for $C_{48}H_{52}ClCoN_4O_2$: 810. found 775 [M-Cl]$^+$.

Example 9

Synthesis of Cobalt (III) Mesoporphyrin IX Dimesylate (9-1)

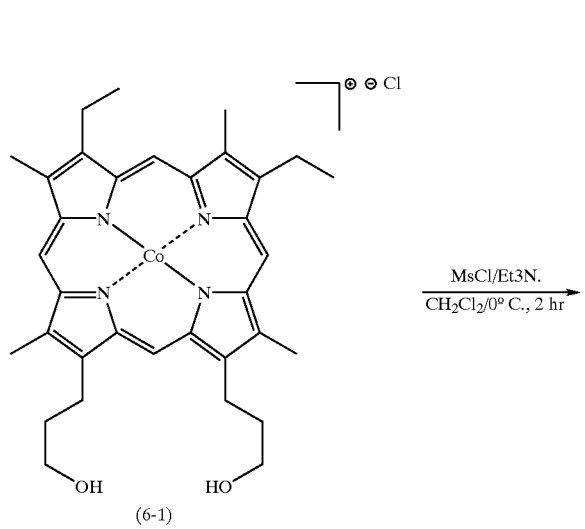

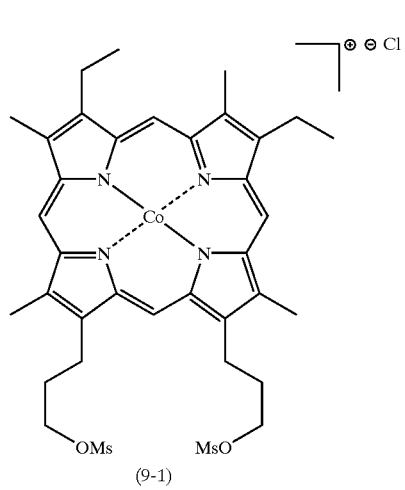

To a solution of cobalt mesoporphyrin diol (6-1) (0.15 g, 0.24 mmol) in dry $CH_2Cl_2$ (4 ml) at 0° C. under argon was added $Et_3N$ (190 μL, 1.43 mmol) and DMAP (0.003 g, 0.024 mmol). A solution of MsCl (74 μL, 0.95 mmol) in dry $CH_2Cl_2$ (0.5 ml) was added (very slowly for 15 min) and stirred for 2 hrs. The reaction was quenched with water (20 ml) and diluted with $CH_2Cl_2$ (10 ml). The organic layer was separated and washed with sat. $NaHCO_3$ (10 ml×1), water (20 ml×1), brine (30 ml×1), dried over $Na_2SO_4$, and concentrated. The crude product (9-1) was obtained as a red solid (0.18 g, 96% yield, >95% pure by LCMS). LCMS. Calc'd for $C_{38}H_{44}ClCoN_4O_4$: 786. found 751 $[M-Cl]^+$.

Example 10

Synthesis of Cobalt (III) Mesoporphyrin IX Dithiobenzyl Ether (10-1)

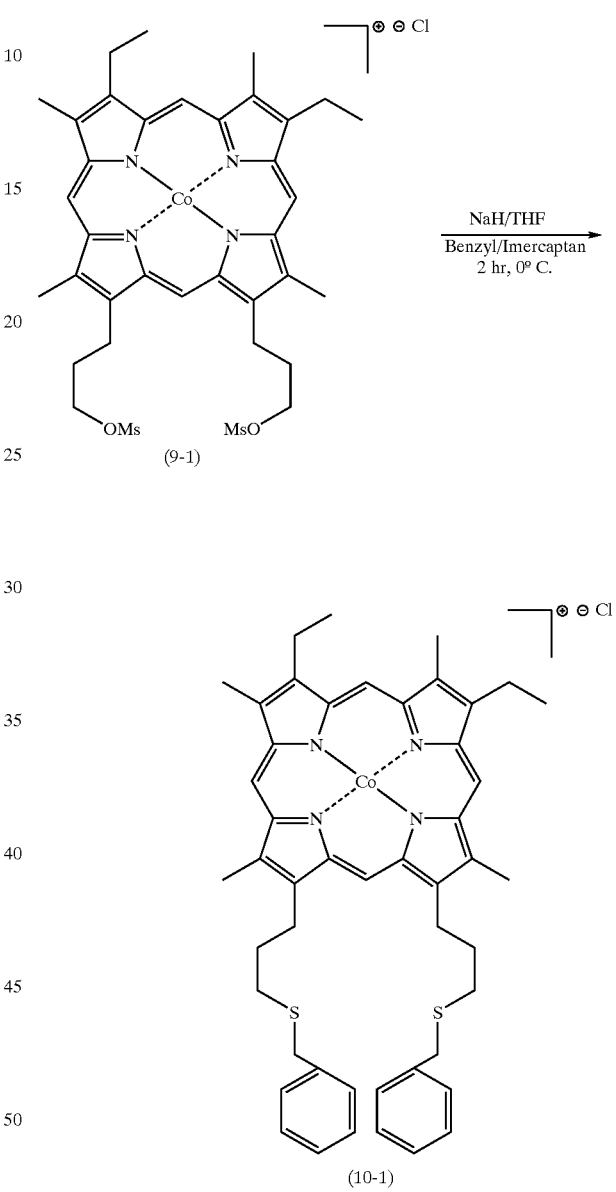

To a suspension of sodium hydride (0.01 g, 0.38 mmol) in dry THF (2 ml) at 0° C. under argon was added a solution of benzyl mercaptan (32 μL, 0.25 mmol) in THF (0.5 ml) slowly. After 30 min, a solution of cobalt mesoporphyrin dimesylate (9-1) (0.05 g, 0.063 mmol) in dry THF (0.5 ml) was added slowly and the reaction mixture was stirred at 0° C. for 2 hrs. The reaction was quenched with water (20 ml) and diluted with ethyl acetate (30 ml). The organic layer was separated and washed with water (20 ml×1), brine 20 ml×1), dried over $Na_2SO_4$ and concentrated. The crude product (10-1) was obtained as a red solid (0.058 g, 110% yield). LCMS. Calc'd for $C_{48}H_{52}ClCoN_4S_2$: 842. found 807 $[M-Cl]^+$.

Example 11

Synthesis of Cobalt (III) Mesoporphyrin IX (11-1)

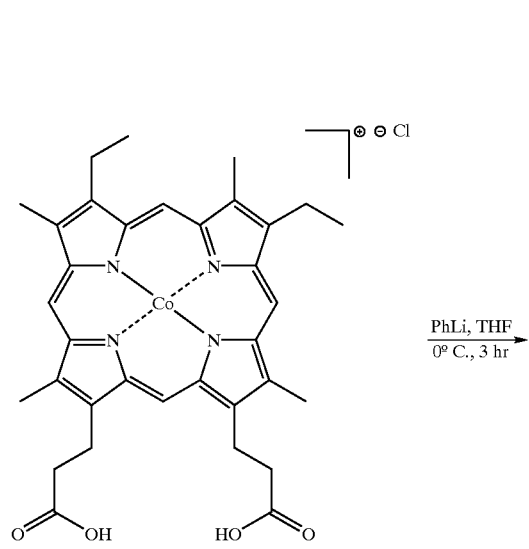

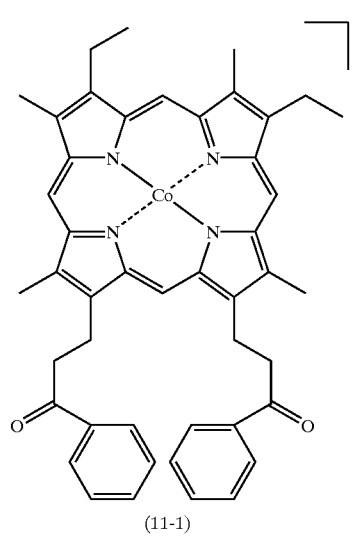

(11-1)

Cobalt (III) mesoporphyrin IX, chloride salt (Porphyrin Products, Inc., Logan, Utah) (0.05 g, 0.078 mmol) was dissolved in dry THF (2 ml) and cooled to 0° C. under argon atmosphere. Phenyl lithium (879 μL, 1.8 M in hexanes, 1.5 mmol) in THF (1 ml) was slowly added over 5 min. After 2 hrs, TMSCl (400 μL, 3 mmol) was quickly added and stirred for an additional 1 hr and allowed to warm to room temperature. The mixture was diluted with 1N HCl (30 ml) and extracted with ethyl acetate (20 ml×3). The combined organic layer was washed with water (20 ml×1), brine (20 ml×1), dried over $Na_2SO_4$, and concentrated. The crude product (11-1) was obtained as a red solid (0.058 g, 98% yield, >75% pure by LCMS).

Example 12

Synthesis of Cobalt (III) Mesoporphyrin IX (12-1) and (12-2)

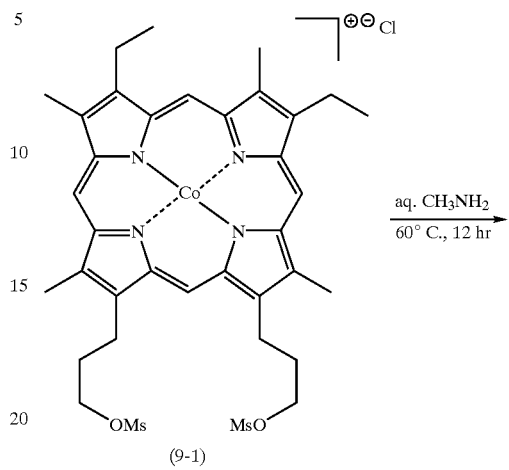

(9-1)

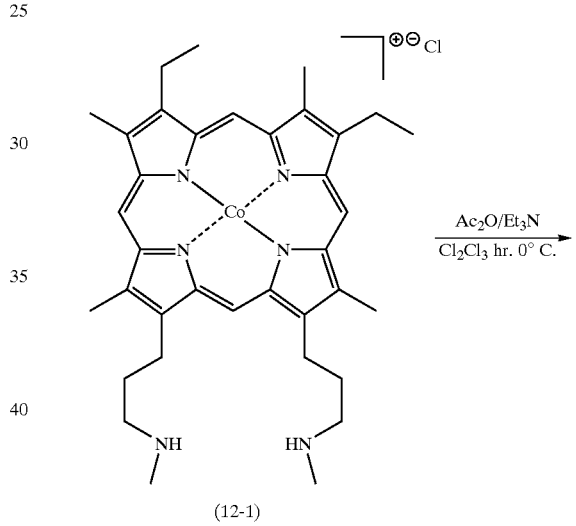

(12-1)

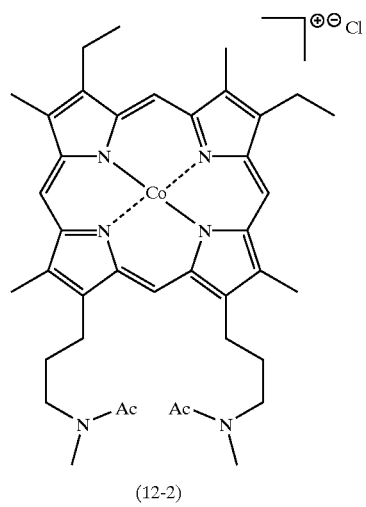

(12-2)

To a solution of cobalt mesoporphyrin dimesylate (9-1) (0.03 g, 0.038 mmol) in methanol (1 ml) was added a solution of methylamine (380 µL, 2 M in methanol, 0.76 mmol) and the reaction mixture was stirred at 60° C. for 12 hrs. The solvent was removed under vacuum, residue was dissolved in $CH_2Cl_2$ (30 ml), washed with water (20 ml×1), brine (20 ml×1), dried over $Na_2SO_4$ and concentrated. The crude product (12-1) was obtained as a red solid (0.023 g). LCMS. Calc'd for $C_{36}H_{46}ClCoN_6$: 656. found 621 [M-Cl]$^+$.

To a solution of cobalt mesoporphyrin (12-1) (0.025 g, 0.038 mmol, ca. 50% pure) in dry $CH_2Cl_2$ (3 ml) at 0° C. under argon atmosphere was added $Et_3N$ (78 µL, 0.61 mmol) and acetic anhydride (31 µL, 0.3 mmol). The mixture was stirred at 0° C. for 3 hrs and quenched with water (20 ml) and diluted with $CH_2Cl_2$ (10 ml). The organic layer was separated, washed with brine (30 ml×1), dried over $Na_2SO_4$ and concentrated. The crude product (12-2) was obtained as a red solid (0.023 g). LCMS. Calc'd for $C_{40}H_{52}ClCoN_6O_2$: 740. found 705 [M-Cl]$^+$.

Example 13

Synthesis of Cobalt (III) Mesoporphyrin IX (13-1)

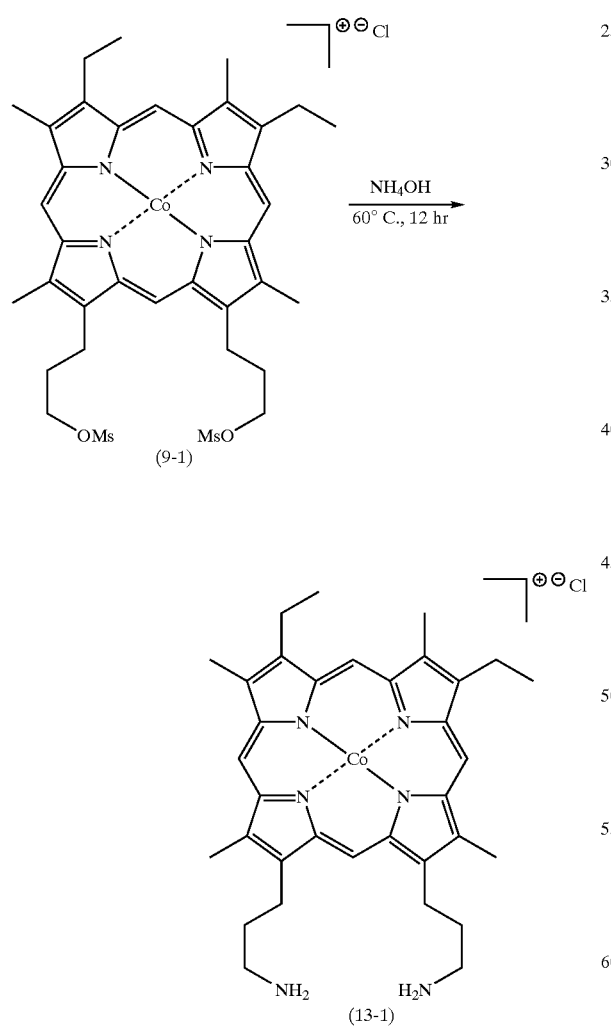

To a solution of cobalt mesoporphyrin dimesylate (9-1) (0.03 g, 0.038 mmol) in methanol (1 ml) was added ammonium hydroxide (90 µL, 30% in water, 0.76 mmol) and stirred at 60° C. for 12 hrs. The solvent was removed under vacuum, residue was dissolved in $CH_2Cl_2$ (30 ml), washed with water (20 ml×1), brine (20 ml×1), dried over $Na_2SO_4$ and concentrated. The crude product (13-1) was obtained as a red solid (0.023 g). LCMS. Calc'd for $C_{34}H_{42}ClCoN_6$: 628. found 593 [M-Cl]$^+$.

Example 14

Synthesis of Cobalt (III) Mesoporphyrin IX (14-1)

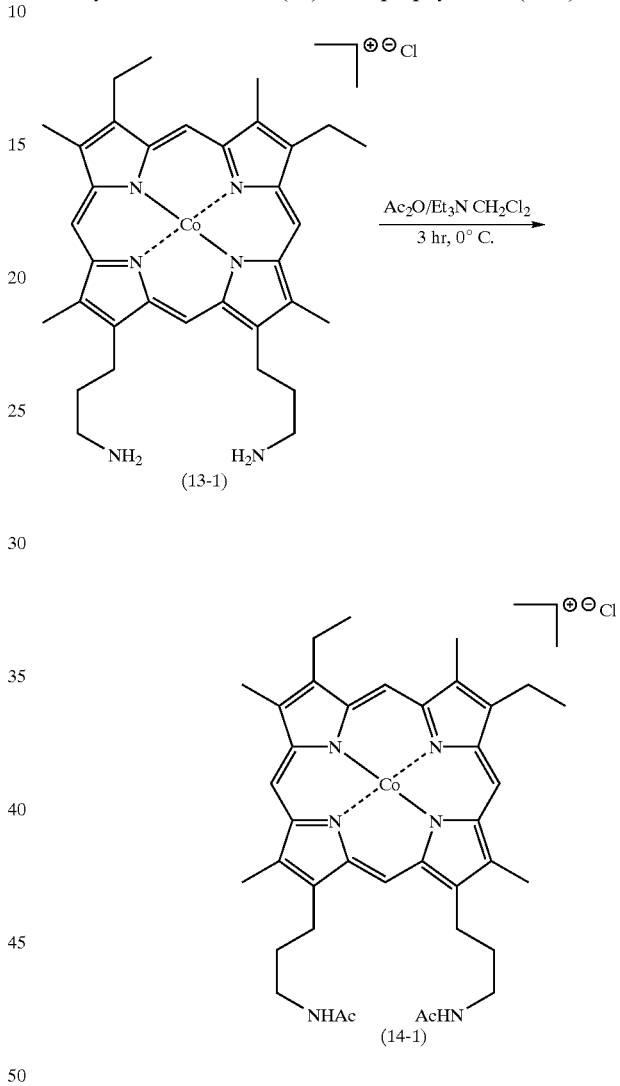

To a solution of the crude cobalt mesoporphyrin (13-1) (0.020 g, 0.032 mmol, ca. 10% pure) in dry $CH_2Cl_2$ (2 ml) at 0° C. under argon atmosphere was added $Et_3N$ (33 µL, 0.25 mmol) and acetic anhydride (13 µL, 0.13 mmol). The mixture was stirred for 3 hrs and was quenched with water (30 ml) and diluted with $CH_2Cl_2$ (30 ml). The organic layer was separated, washed with brine (20 ml×1), dried over $Na_2SO_4$ and concentrated. The crude product (14-1) was obtained as a red solid (0.020 g). LCMS. Calc'd for $C_{38}H_{46}ClCoN_6O_2$: 712. found 677 [M-Cl]$^+$.

Example 15

Cellular Assay for Generation of Reactive Oxygen Species (ROS)

All cell culture reagents were incubated in a water bath at 37° C. for approximately 30 minutes. Existing media from a near confluent tissue culture flask containing SH-SY5Y neuroblastoma cells was aspirated using a flame sterilized glass transfer pipette attached to a trapped vacuum apparatus. Calcium free PBS buffer was pipetted into the tissue culture flask (2 ml for a 75 cm2 flask, 3 ml for a 175 cm$^2$ flask). The flask was tipped slightly to ensure that the buffer covers the cell culture and then the buffer was removed by aspiration. Trypsin media was pipetted into the tissue culture flask (2 ml for a 75 cm$^2$ flask, 3 ml for a 175 cm$^2$ flask) and evenly spread to ensure that the trypsin covered the cell culture. The cell culture was incubated with trypsin media for 4–6 minutes at room temperature. After cells were released from the flask, the flask was tilted to one corner. Using the existing media within the flask, the aggregated cells were collected towards one corner and repeatedly pipetted to obtain a single cell suspension. The cell suspension was transferred with a pipette into a 15 ml conical shaped centrifuge tube then cell culture media was added to the suspension up to a total volume of 14 ml. Ten $\mu$l aliquots were withdrawn and the cells were counted using a hemocytometer. The suspension was centrifuged at 200×g for 10 minutes, the supernatant was aspirated off, and the cell pellet was resuspended at $3.75 \times 10^5$ cells/ml in cell culture medium. Two hundred $\mu$l of cell suspension were aliquoted per well in the 96 well dish to obtain a final cell number of 75,000 cells per well. The plates were incubated overnight at 37° C. and 5% $CO_2$ in a humidified cell incubator.

The medium was carefully removed from the wells by aspiration with an 18 g needle. The wells were gently rinsed once with 200 $\mu$l of warm Hanks balanced saline solution (HBSS, Gibco-BRL). 200 $\mu$l of 30 $\mu$M dichlorofluorescin-diacetate (DCFC-DA) was added to each well and the cells were incubated for 1 hour at 37° C. under 5% $CO_2$ in a humidified cell incubator. The excess DCFC-DA was removed by needle aspiration and each well was gently rinsed twice with 200 $\mu$l of warm Hank's Balanced Salt Solution (HBSS).

Stock solutions of test compound, such as Co-PP, Co-MP, or a Co-P of this invention, and of an $H_2O_2$ scavenger such as ebselen, were typically prepared in dimethylformamide or dimethylsulfoxide and diluted further into working concentrations using HBSS. The final concentration of the organic solvents were kept at or below 0.1% when on cells. Eighty $\mu$l of HBSS was aliquoted into the well and 20 $\mu$l of test compound solution in HBSS. The plate was read immediately in Cytofluor model 2350 system (Millipore; excitation wavelength: 485 nm; emission wavelength: 530 nm) for a 0 min timepoint reading. The cells were incubated for 30 minutes at room temperature with test compound following which a 30 min reading was taken. The change in RMF over the 30 minutes period was calculated for each well. The well media was removed by needle aspiration and 15.6 $\mu$l of 37% formaldehyde was added to each well. The cells were incubated for 2–10 min and washed with 200 $\mu$l of $H_2O$. Then 100 $\mu$l of a 10 $\mu$g/ml aqueous solution of Hoechst 33342 was added to each well and the plate was kept in the dark for 10 min. The plate was then read in the Cytofluor (excitation wavelength: 360 nm; emission wavelength: 460 nm) and the Hoechst fluorescence values were used to normalize the DCFC-DA RMF data.

Figure 2:
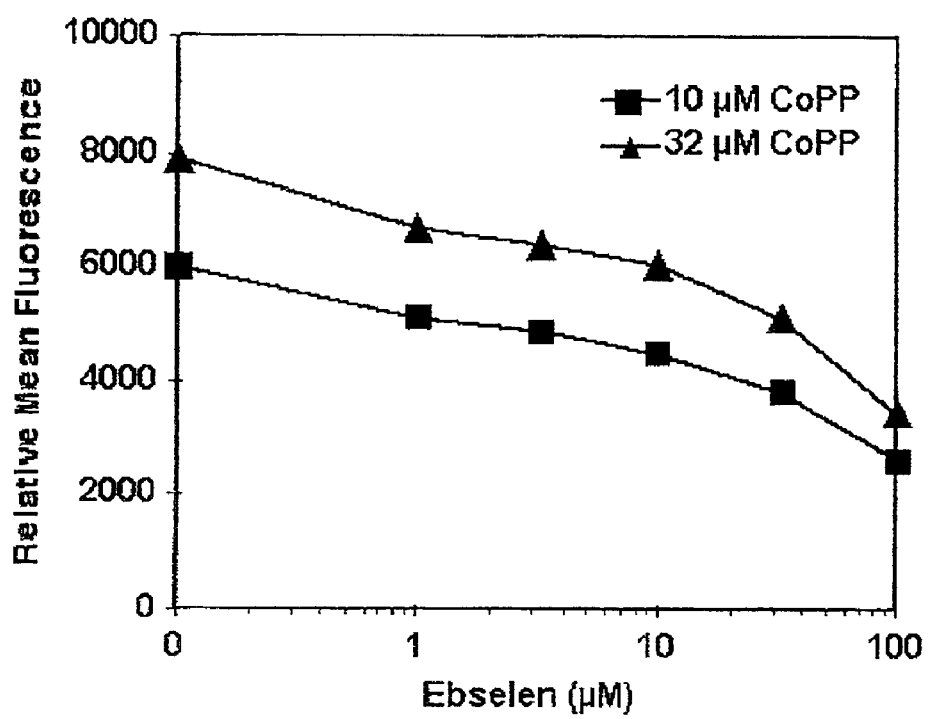
FIG. 2 illustrates that addition of the glutathione peroxidase mimic, ebselen, scavenges the reactive oxygen species induced in SH-SY5Y cells by Co-PP and Co-MP.
Figure 3:
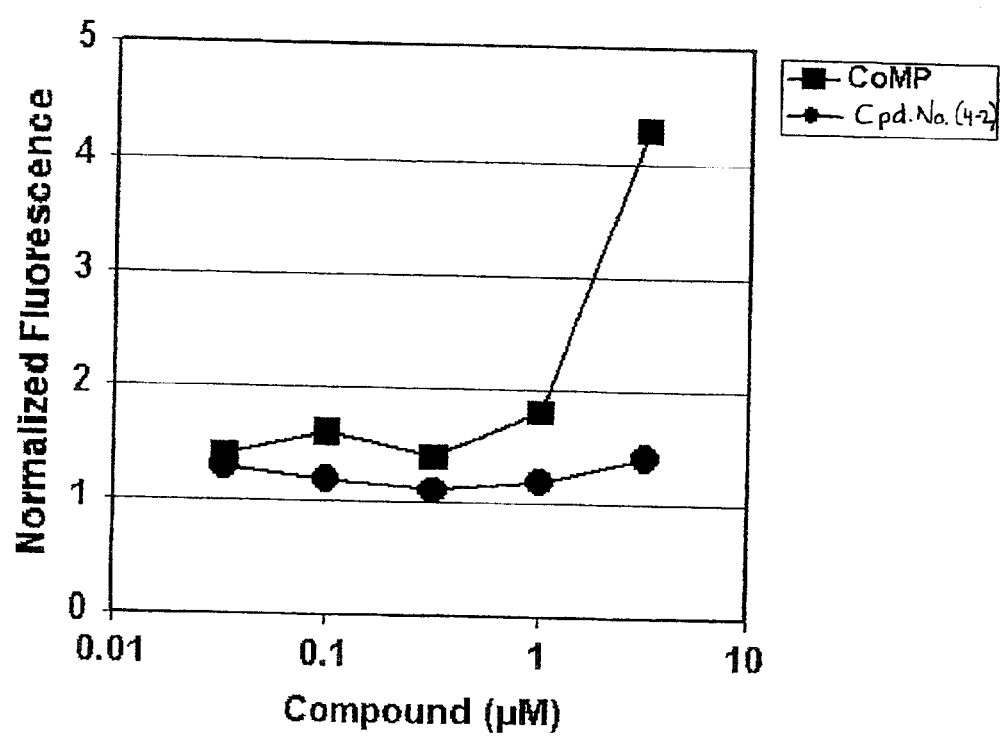
FIG. 3 illustrates that a representative Co-P complex of this invention does not trigger ROS generation in SH-SY5Y cells.

As illustrated in FIG. 1, reactive oxygen species were induced by Co-PP and Co-MP in SH-SY5Y cells. However, as illustrated in FIG. 2, addition of a glutathione peroxidase mimetic, ebelsen, scavanges the reactive oxygen species induced in SH-SY5Y cells by Co-PP and Co-MP. Administration of a representative Co-P of this invention—that is, compound (4-2) of Example 4—does not trigger generation of reactive oxygen species in SH-SY5Y cells compared to Co-PP, as illustrated in FIG. 3.

Example 16

Measurement of Oxygen Consumption Catalyzed by Co-P in the Presence of Ascorbate/TMPD Ten mM stock solutions of a Co-P of this invention (i.e., test compound) were prepared using ethanol as solvent. KCl media consists of 125 mM KCl, 2 mM $K_2HPO_4$, 20 mM HEPES, pH 7.0. Oxygen consumption measurements were carried out using a Clark type oxygen electrode (Rank Brothers Ltd., Cambridge, UK) and assay solutions were magnetically stirred during the course of the experiments. To 500 $\mu$l of assay solution (KCl media supplemented with 2 mM sodium ascorbate and 40 $\mu$M N,N,N',N'-1,4-tetramethylenediamine (TMPD)) is added 2 $\mu$l of a stock solution of test compound (40 $\mu$M final concentration) and the oxygen consumption rate is followed for 2–4 min. Subsequently, a 5 $\mu$l aliquot of a freshly made catalase solution (100 mg/ml solution in KCl media) is added to determine if $H_2O_2$ is generated via redox cycling of the test compound.

Figure 4:
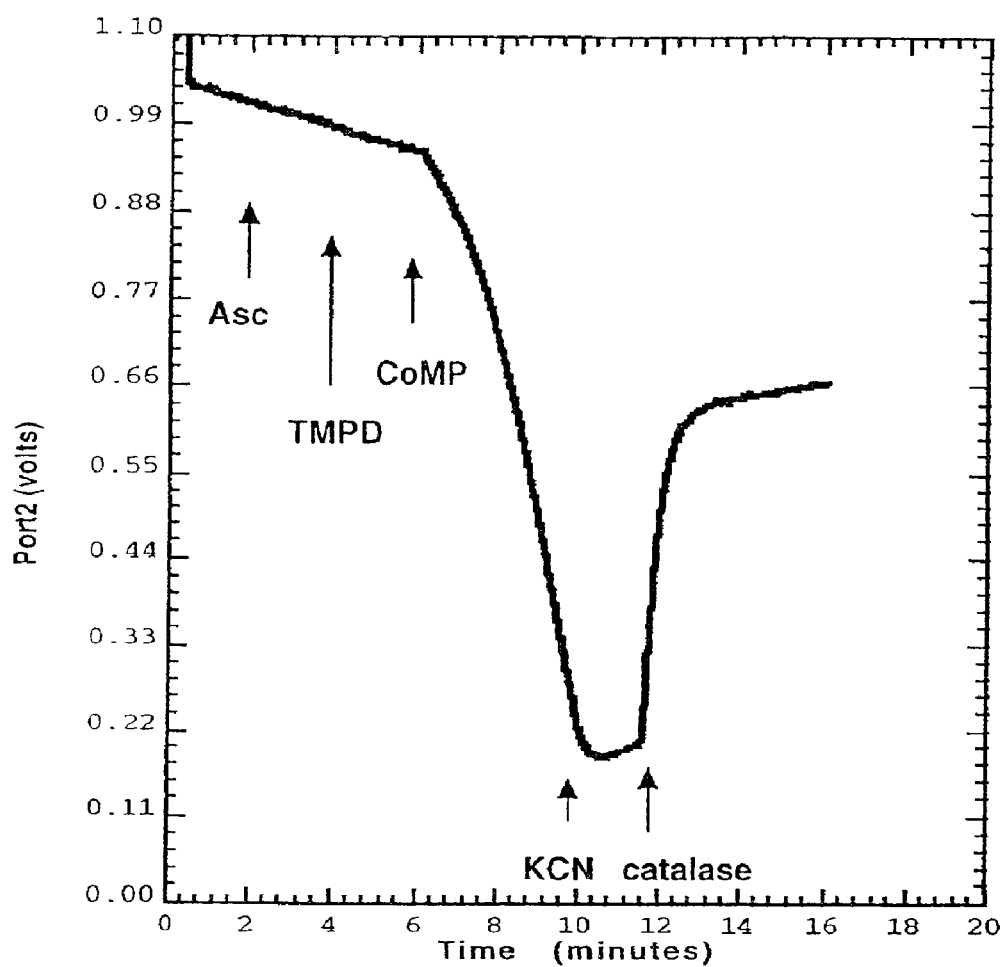
FIG. 4 illustrates Co-MP catalyzed $O_2$ consumption in the cell free ascorbate/TMPD system.
Figure 5:
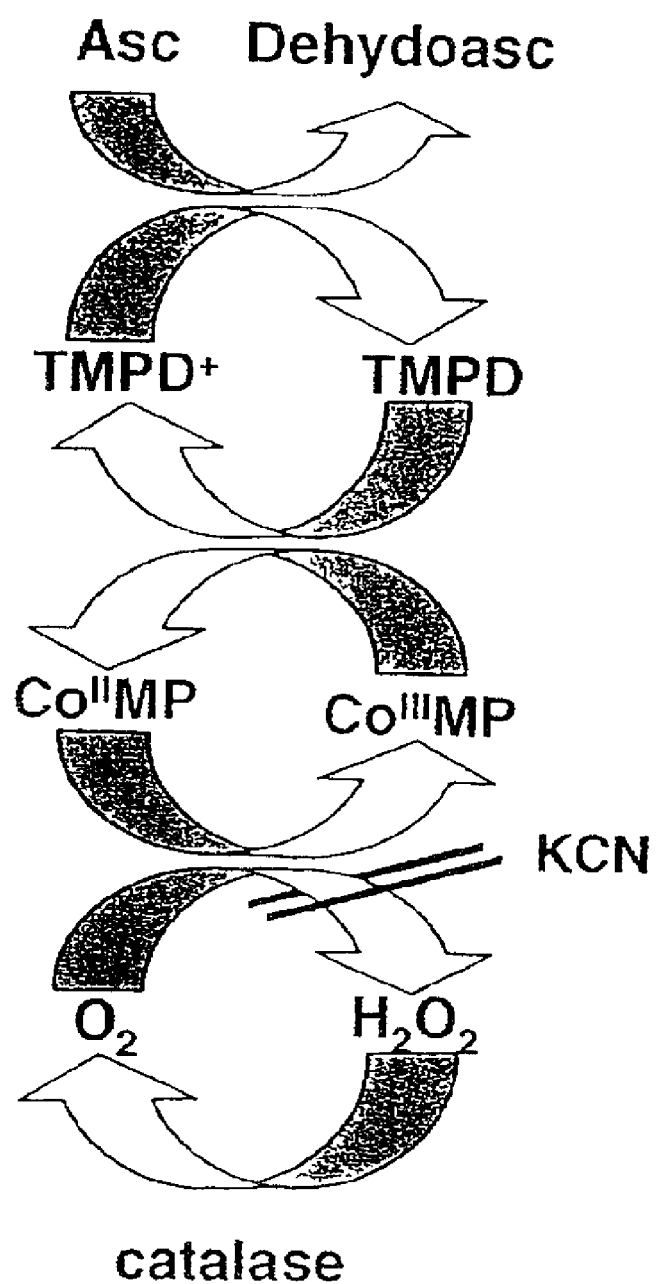
FIG. 5 illustrates a possible reaction scheme for Co-MP-catalysed oxygen consumption.

FIGS. 4 and 5 illustrate the reaction time course and proposed reaction mechanism for oxygen consumption, respectively. Initial rates are calculated from oxygen consumption slopes and rate of a solvent control is subtracted. Rates for tested compounds are normalized to the rate obtained for the chloride salt of Co-MP (assigned a relative rate of 1) More specifically, FIG. 4 shows Co-MP catalyzed $O_2$ consumption in cell free ascorbate/TMPD system. An aliquot of a 10 mM stock solution of Co-MP (final concentration of 40 $\mu$M) was added to assay buffer containing 2 mM of ascorbate and 40 $\mu$M of TMPD. There was an immediate depletion of dissolved $O_2$ in the cuvette as detected by Clark oxygen electrode. $CN^-$, a strong ligand for cobalt ion, strongly inhibits the redox reaction. Addition of catalase results in conversion of $H_2O_2$ present in the assay solution to $O_2$ and $H_2O$. FIG. 5 illustrates a possible reaction scheme for Co-MP—catalysed oxygen consumption—that is, Co-MP accepts electrons from ascorbate via TMPD and carries out the reduction of dissolved $O_2$ to $H_2O_2$; $CN^-$ competes with $O_2$ for cobalt and inhibits the reduction reaction; in the presence of catalase, $H_2O_2$ produced in the reaction is converted to $O_2$ and $H_2O$.

Figure 6:
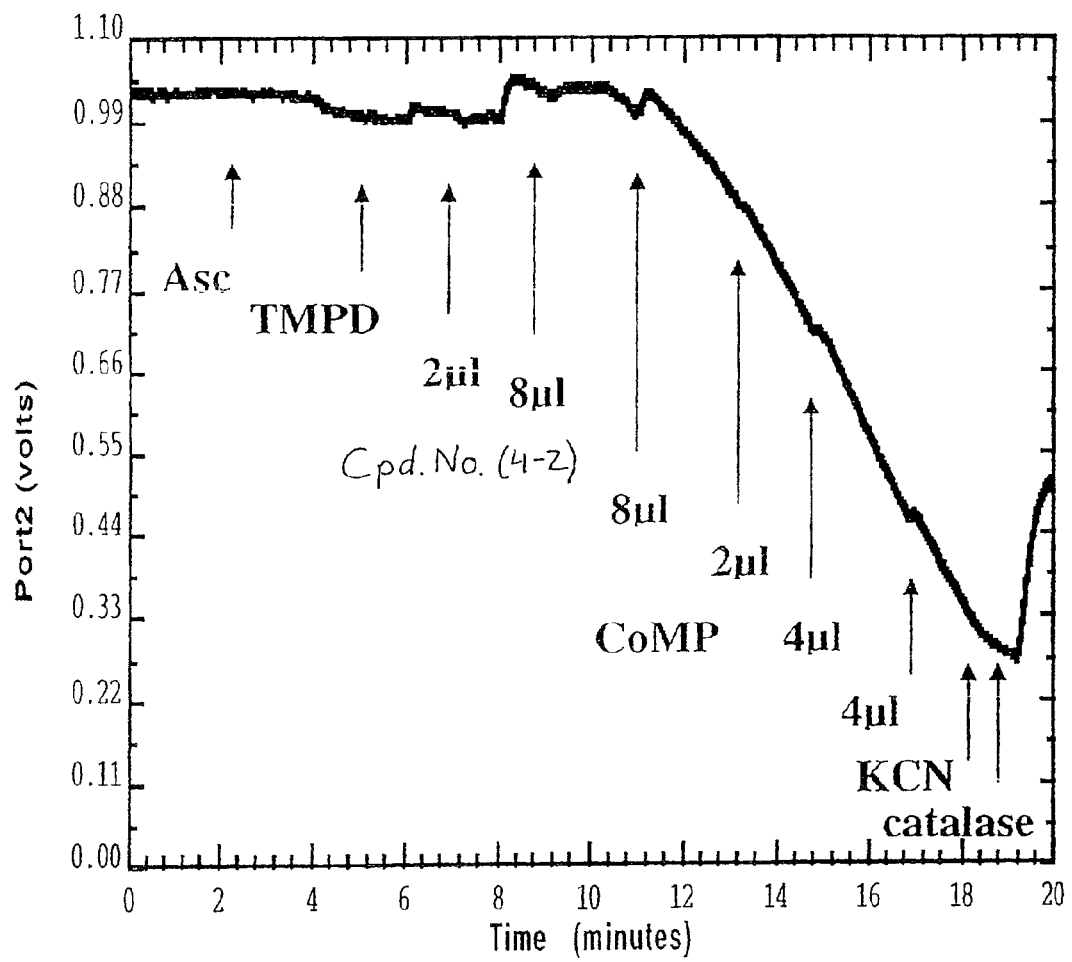
FIG. 6 illustrates that a representative Co-P complex of this invention does not redox cycle in the cell free Ascorbate/TMPD system

Referring to FIG. 6, a representative Co-P complex of this invention, Compound No. (4-2), does not redox cycle in the cell free ascorbate/TMPD system. Stock solutions of the test compound were at 10 mM. Aliquots of the stock solutions were added to 500 $\mu$l of assay buffer containing 2 mM of ascorbate and 40 $\mu$M of TMPD. Addition of Compound No. (4-2) does not result in any $O_2$ consumption. However, addition of Co-MP triggers robust consumption of $O_2$ in the assay solution.

Example 17

Oxidation of Reduced Cytochrome C by Co-PP

Figure 7:
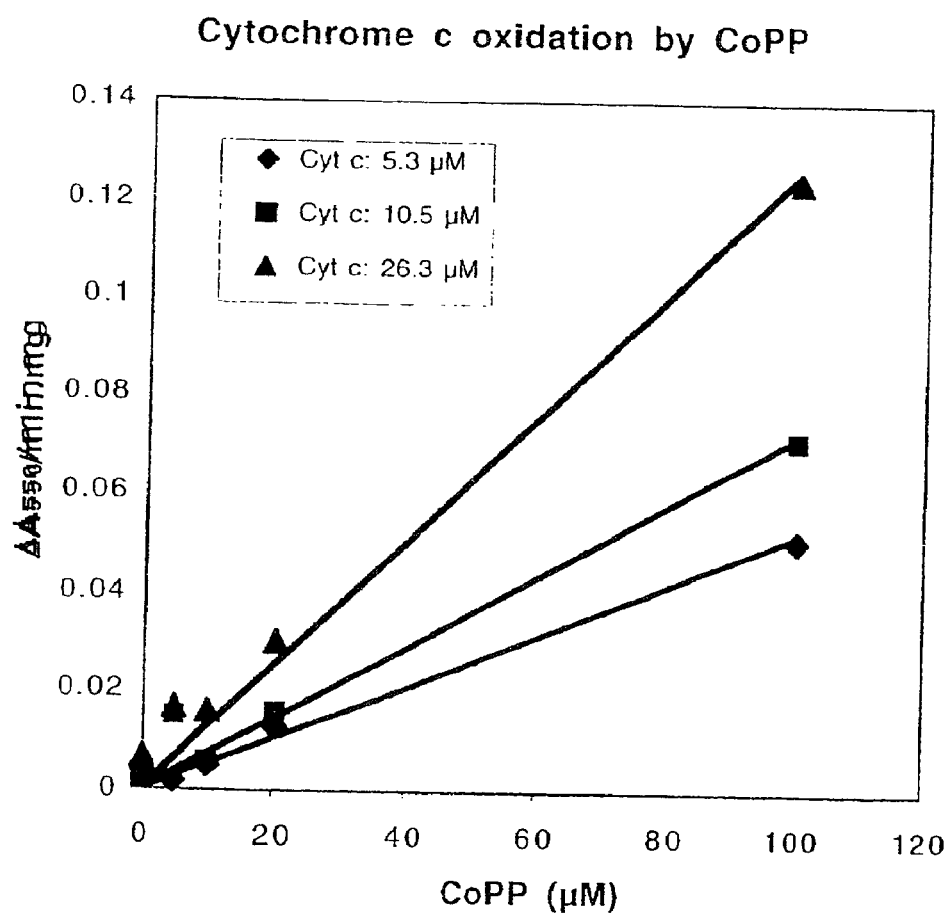
FIG. 7 illustrates oxidation of reduced cytochrome c by Co-PP.
Figure 8:
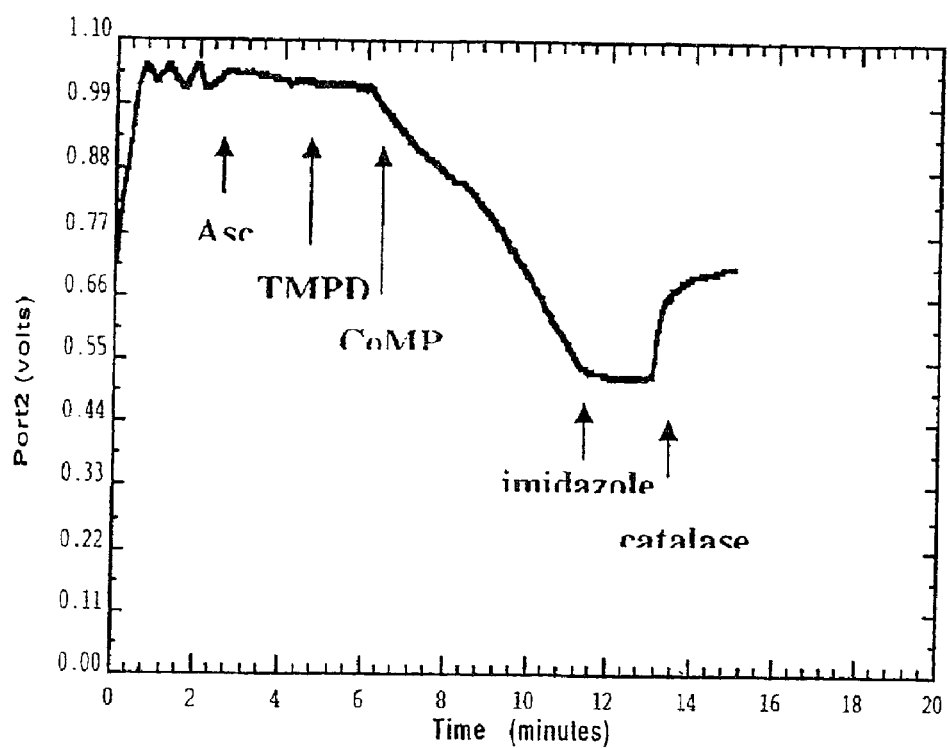
FIG. 8 illustrates that a representative ligand of this invention, imidazole, does not redox cycle in the cell free Ascorbate/TMPD system.

Reduced cytochrome c was prepared by the addition of an excess of ascorbic acid to a solution of cytochrome c and allowing the solution to stand for 5 to 10 minutes. The reduced protein was purified over a Sephadex G50 column and checked spectrophotometrically by measuring absorbance at 550 nm, followed by the addition of a few grains of dithionite and measuring absorbance again at 550 nm. The extinction coefficient for fully reduced cytochrome c is 29 mM$^{-1}$. Initial rates of oxidation of reduced cytochrome c at three concentrations (5.3 μM, 10.5 μM and 26 μM) were followed in the presence of 0, 5,10, 20 and 100 μM CoPP. Assays were conducted in 1 ml of assay buffer (20 mM potassium phosphate, pH 7.0, 0.2 mg/ml dodecyl-β-maltoside) and initiated by the addition of desired concentration of reduced cytochrome c and monitoring the change in absorbance at 550 nm for 90 seconds. The fully oxidized absorbance value was determined by the addition of a few grains of ferricyanide to the cuvette. FIG. 7 shows that Co-PP serves as an electron acceptor from reduced cytochrome c. In a biological system, Co-PP can transfer electrons from an electron rich donor/reductant to molecular oxygen, $O_2$, to generate reactive oxygen species, the production of which can be toxic to cells and give rise to undesirable side effects (e.g. oxidative stress).

Example 18

Measurement of Oxygen Consumption Catalyzed by Co-P in the Presence of Ascorbate/TMPD Representative Co-P compounds of this invention were prepared by the procedures disclosed above, and assayed by the procedure of Example 16 to measure oxygen consumption catalyzed by the test compound in the presence of ascorbate/TMPD. As shown in FIG. 7, a strong ligand to Co-PP (i.e., imidazole) blocks generation of reactive oxygen species. The above procedure was then repeated for other representative Co-P compounds of this invention, but utilizing different ligands and/or R groups. The results of these experiments are presented in Tables 1 through 3 below.

TABLE 1

Effect of Ligand on Oxygen Consumption of Co-MP

| $L_1 = L_2$ | Relative Rate |
|---|---|
| Cl$^-$ | 1 (assigned value) |
| CN$^-$ | <0.05 |

TABLE 1-continued

| | |
|---|---|
| imidazole (NH) | 0.04–0.09 |
| $H_2N$–CH$_2$–COO$^-$ (glycine) | 0.71–1.5 |
| MeO–C$_6$H$_4$–CH$_2$–NH2 | 0.06 |

TABLE 2

Effect of Ligand and $R_5$ Moiety on Oxygen Consumption of Co-MP

| $R_5$ (both) | $L_1 = L_2$ | Relative Rate |
|---|---|---|
| H | Cl$^-$ | 1 (assigned value) |
| CH$_3$ | Cl$^-$ | 0.05–0.07 |
| CH$_3$ | imidazole (NH) | (not detected) |
| CH$_3$ | $H_2N$–CH$_2$–COO$^-$ | 0.21 ± 0.04 |
| CH$_3$ | $H_2N$–CH$_2$–CO$_2$CH$_3$ | 0.08 |

TABLE 3

Effect of Ligand, $R_5$ and A Moiety on Oxygen Consumption of Co-MP

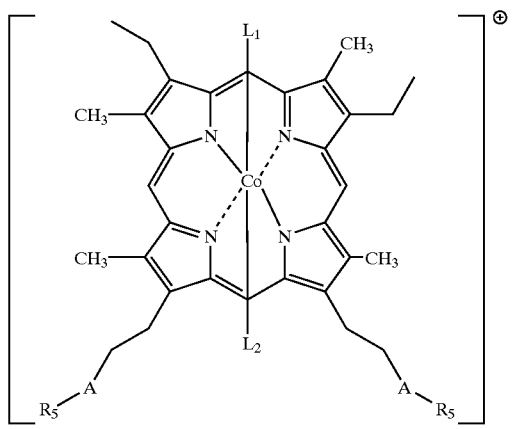

| Compound | A | $L_1 = L_2$ | $R_5$ (both) | Relative Rate |
| --- | --- | --- | --- | --- |
| Co-MP | —C(=O)O— | Cl⁻ | —H | 1 (assigned value) |
| Co-PP | —C(=O)O— | Cl⁻ | —H | 2.2 |
| (1-1) | —C(=O)O— | H₂N⌒COO⁻ | —CH₃ | 0.21 ± 0.04 |
| (1-2) | —C(=O)O— | H₂N⌒COO⁻ | -nBu | (not detected) |
| (1-3) | —C(=O)O— | H₂N⌒COO⁻ | -iBu | (not detected) |
| (1-4) | —C(=O)O— | H₂N⌒COO⁻ | -iAmyl | (not detected) |
| (1-5) | —C(=O)O— | H₂N⌒COO⁻ | -Et | 0.08 ± 0.01 |
| (1-6) | —C(=O)O— | H₂N⌒COO⁻ | -iPr | (not detected) |
| (4-2) | —C(=O)NH— | imidazole-NH | —CH₂(4-methoxyphenyl) | (not detected) |

TABLE 4

Effect of Ligand, $R_5$, A and n Moiety on Oxygen Consumption of Co-MP

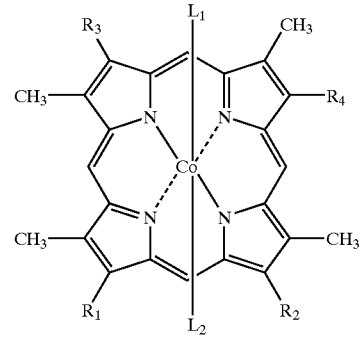

| Compound | n | A | $L_1 = L_2$ | $R_5$ (both) | Relative Rate |
|---|---|---|---|---|---|
| Co-MP | 2 | —C(=O)O— | $Cl^-$ | —H | 1.0 (assigned value) |
| (6-1) | 3 | —O— | $Cl^-$ | —H | 0.56 |
| (7-1) | 3 | —OC(=O)— | $Cl^-$ | —$CH_3$ | 0.07 |
| (8-1) | 3 | —O— | $Cl^-$ | benzyl | 0.045 |
| (10-1) | 3 | —S— | $Cl^-$ | benzyl | 0.021 |
| (11-1) | 2 | —C(=O)— | $Cl^-$ | phenyl | 0.0005 |

Example 19

Weight Loss and Lesion Severity Assays

Male Sprague Dawley rats (approximately 200 g) were purchased from Charles River Canada, Inc. and were shipped to the Animal Care Facility at the University of Vermont. Upon arrival they were housed in separate cages with corncob bedding and ad lib access to tap water and purina rat chow. The animal facility is maintained at a temperature of 71° F. +/−1° F. with a 12-hour light/dark cycle, lights on at 6:00 am and off at 6:00 pm. Two days later (Day-3) all rats were shaved in the nuchal area and baseline color photographs of the nuchal area were taken (light halothane anesthesia was utilized to facilitate the shaving). Three days later (Day 0) experimental compounds were made up at 12 mM concentrations in vehicle (i.e., saline:PEG400:EtOH (5:4:1), pH 7.4). Animals were injected subcutaneously in the nuchal area with the various stock solutions at a dose of 400 µl per 100 grams body weight. Typical injection volumes, therefore, range from 1 to 1.5 ml per animal. Animals were injected using a modified Z-track technique to try and minimize outflow of injected compounds due to the high volume utilized. Each animal was weighed prior to injection and all injections were accomplished in an approximately two-hour period. No anesthesia was utilized for injections.

Animals subsequently underwent daily weighing with a Mettler 6 second integrating balance and had ad lib access to tap water and purina rat chow. At various intervals after injections, the nuchal area of rats was again photographed. In addition to the photographic record, from the second experiment on, all rats had a daily assessment of the severity of any lesions in the nuchal area. The scale used was 0 for no lesions, 5 for the worst lesions with breakdown of the skin and open flow of exudates. Grades in-between were estimated by the operator based on the size and severity of the lesion. In those cases where animals had a grade 5 lesion, either individuals animals were euthanized or the experiment was terminated rapidly after the appearance of such lesions. After 8 days, final photographs were taken and all animals were euthanized, marking the end of the experiment.

Figure 9A:
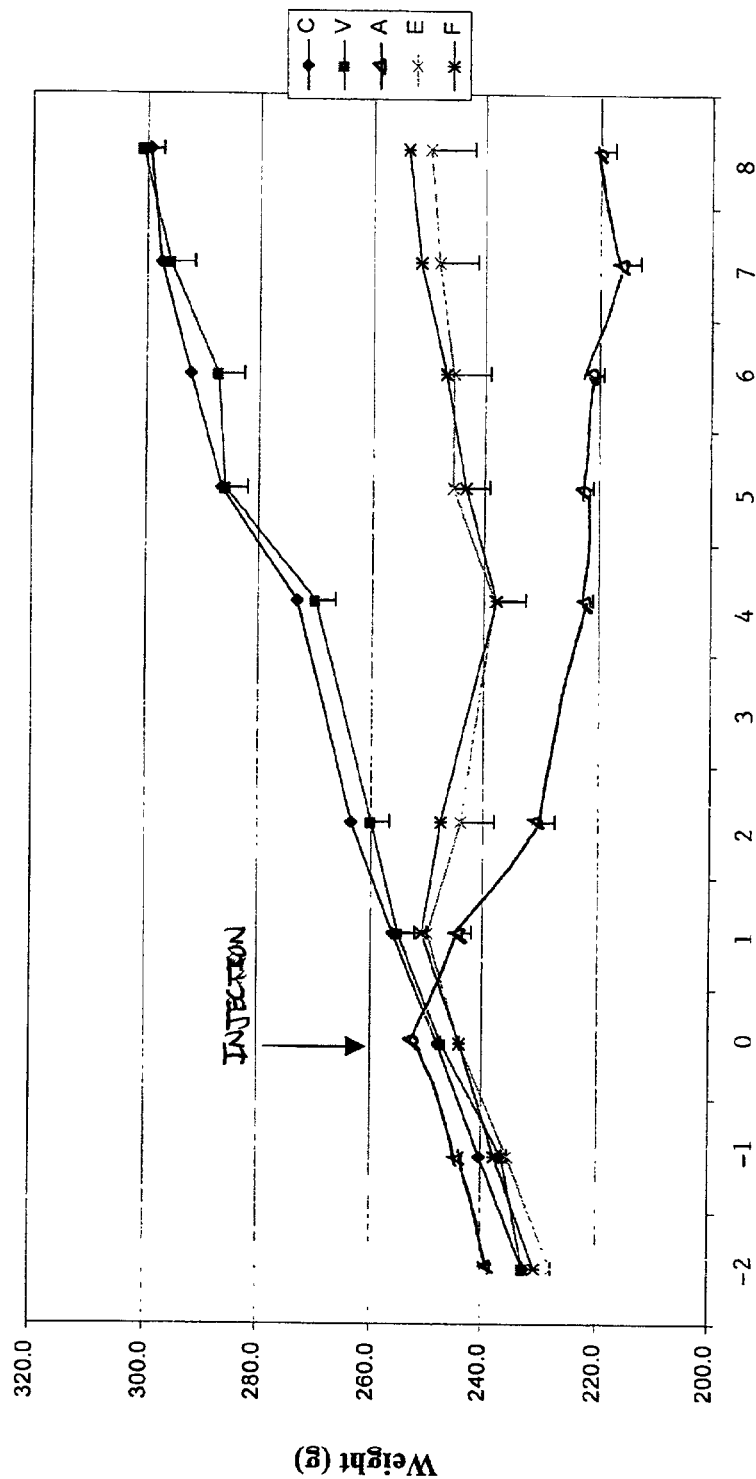
FIGS. 9A and 9B illustrate weight loss (FIG. 9A) and lesion severity (FIG. 9B) for representative Co-P complexes compared to Co-MP and a non-injected control and vehicle-injected control.
Figure 9B:
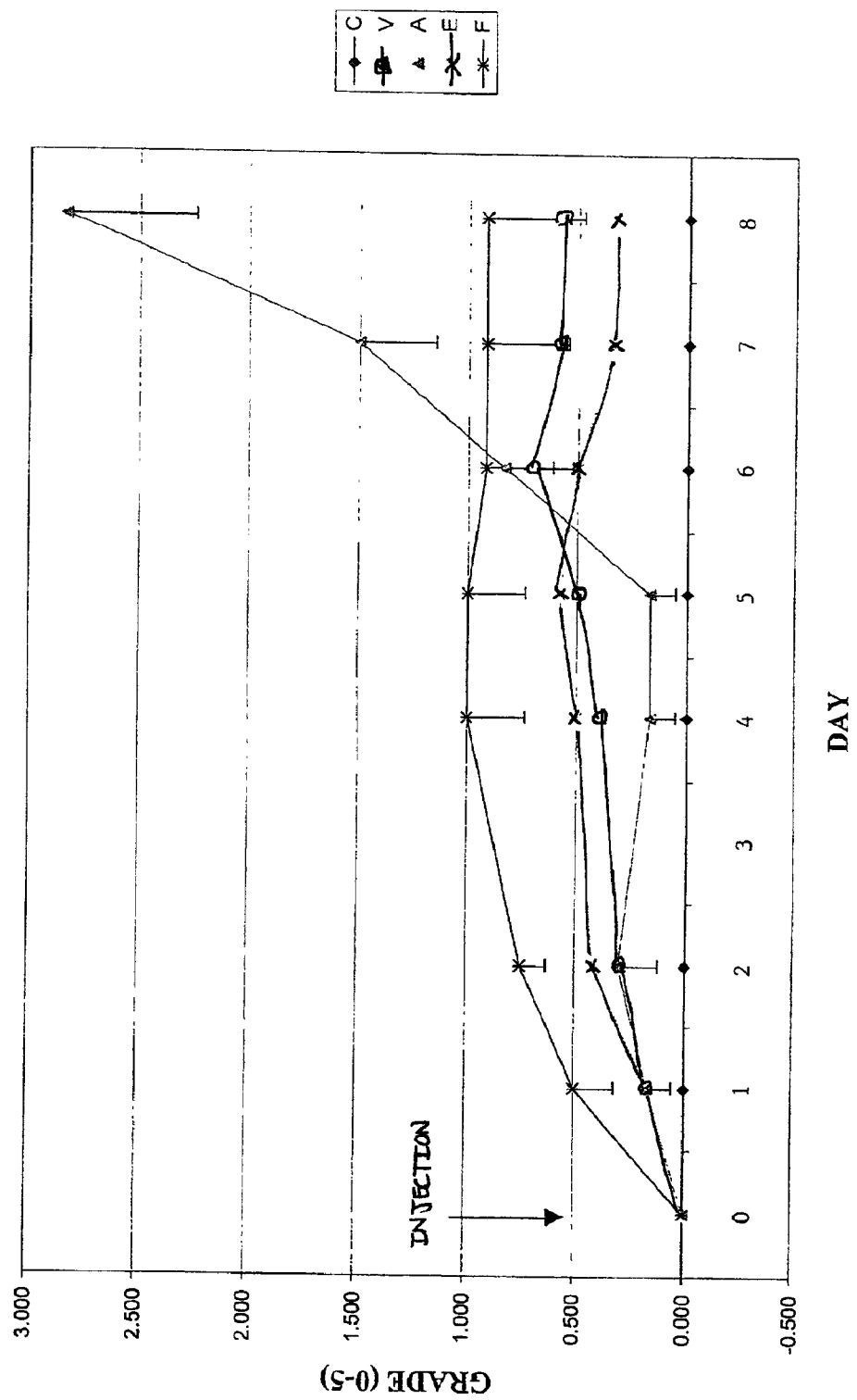

Means of body weights for each group were calculated and plotted over time (FIG. 9A), as were numerical means of the lesion severity index (FIG. 9B). In FIGS. 9A and 9B, C=noninjected control, V=vehicle injected control, A=Co-MP, E=Cpd. No. (1-6) and F=Cpd. No. (4-4). In this experiment, Co-MP yielded the greatest body weight response, but similarly exhibited the greatest lesion severity. Cpd. Nos. (1-6) and (4-4) showed favorable body weight responses and did not exceed grade 1 lesion severity.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed:

1. A cobalt-porphyrin complex having the structure:

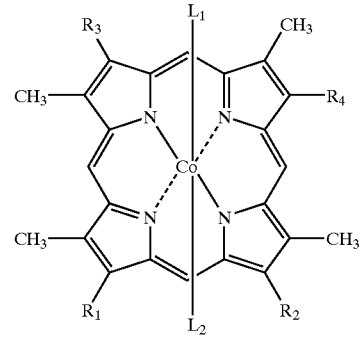

or a salt thereof, wherein:
$R_1$ and $R_2$ are both —$(CH_2)_2C(=O)OCH(CH_3)_2$;
$R_3$ and $R_4$ are both —$CH_2CH_3$; and
$L_1$ and $L_2$ are both glycinate.

2. A composition comprising a compound of claim 1 in combination with a pharmaceutically acceptable carrier.

3. A method for treating obesity, comprising administering an effective amount of a composition comprising a cobalt-porphyrin complex and a pharmaceutically acceptable carrier, wherein the cobalt-porphyrin complex has the structure:

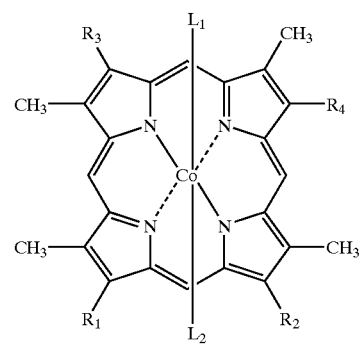

or a salt thereof, wherein:
$R_1$ and $R_2$ are both —$(CH_2)_2C(=O)OCH(CH_3)_2$;
$R_3$ and $R_4$ are both —$CH_2CH_3$; and
$L_1$ and $L_2$ are both glycinate.

* * * * *